US011690927B2

United States Patent
Stibich et al.

(10) Patent No.: US 11,690,927 B2
(45) Date of Patent: Jul. 4, 2023

(54) SYSTEMS, CABINETS AND METHODS FOR DISINFECTING OBJECTS

(71) Applicant: Xenex Disinfection Services LLC., San Antonio, TX (US)

(72) Inventors: Mark Stibich, Santa Fe, NM (US); Deepak Jayaraj, San Antonio, TX (US); Sarah Simmons, San Antonio, TX (US); Paul Froutan, Katy, TX (US); Rodger Mack, New Braunfels, TX (US); Edward Guerrero, San Antonio, TX (US)

(73) Assignee: Xenex Disinfection Services Inc., San Antonio, TX (US)

( * ) Notice: Subject to any disclaimer, the term of this patent is extended or adjusted under 35 U.S.C. 154(b) by 0 days.

(21) Appl. No.: 15/673,033

(22) Filed: Aug. 9, 2017

(65) Prior Publication Data

US 2017/0360977 A1 Dec. 21, 2017

Related U.S. Application Data

(63) Continuation-in-part of application No. PCT/US2017/016675, filed on Feb. 6, 2017, which is
(Continued)

(51) Int. Cl.
*A61L 2/26* (2006.01)
*A61L 2/08* (2006.01)
(Continued)

(52) U.S. Cl.
CPC ............ *A61L 2/26* (2013.01); *A61L 2/08* (2013.01); *A61L 2/10* (2013.01); *A61L 2/14* (2013.01);
(Continued)

(58) Field of Classification Search
CPC ...... A61L 2/26; A61L 2/08; A61L 2/14; A61L 2/18; A61L 2/06; A61L 2/07; A61L 2/10;
(Continued)

(56) References Cited

U.S. PATENT DOCUMENTS 2,615,120 A 10/1952 Macksoud
2,821,982 A * 2/1958 St John Lyburn ..... A61H 33/06
607/87
(Continued)

FOREIGN PATENT DOCUMENTS

CA 2427302 11/2003
CN 87203475 8/1988
(Continued)

OTHER PUBLICATIONS terrauniversal.com, UV Sterilization/Filtration Cabinet, retrieved from internet on May 15, 2015, 1 page.
(Continued)

*Primary Examiner* — Regina M Yoo
(74) *Attorney, Agent, or Firm* — Egan, Enders & Huston LLP.

(57) ABSTRACT

Methods are provided that include positioning a disinfection apparatus in proximity to a cabinet, wherein the disinfection apparatus has a base supporting a germicidal source and the base includes components operationally coupled to the germicidal source for operating the germicidal source. The method further includes inserting the germicidal source into the cabinet such that at least a portion of the base is retained exterior to the cabinet and is operationally coupled to the germicidal source. Moreover, the method includes placing one or more items into the cabinet, closing the cabinet with the germicidal source and the one or more items in the cabinet and the base of the disinfection apparatus exterior to the cabinet, and then subsequently starting the disinfection
(Continued)

source such that the germicidal source emits a germicide into the cabinet. Systems and cabinets used to conduct the aforementioned methods are also provided.

37 Claims, 8 Drawing Sheets

Related U.S. Application Data a continuation-in-part of application No. 15/363,917, filed on Nov. 29, 2016.

(60) Provisional application No. 62/291,024, filed on Feb. 4, 2016.

(51) Int. Cl.
| | |
|---|---|
| *A61L 2/14* | (2006.01) |
| *A61L 2/20* | (2006.01) |
| *A61L 2/18* | (2006.01) |
| *A61L 2/10* | (2006.01) |
| *A61L 2/06* | (2006.01) |
| *A61L 2/07* | (2006.01) |

(52) U.S. Cl.
CPC ............. *A61L 2/18* (2013.01); *A61L 2/20* (2013.01); *A61L 2/06* (2013.01); *A61L 2/07* (2013.01); *A61L 2/202* (2013.01); *A61L 2202/11* (2013.01); *A61L 2202/122* (2013.01); *A61L 2202/15* (2013.01)

(58) Field of Classification Search
CPC ........ A61L 2/20; A61L 2/202; A61L 2202/11; A61L 2202/122; A61L 2202/15
See application file for complete search history.

(56) References Cited

U.S. PATENT DOCUMENTS

| | | | |
|---|---|---|---|
| 3,048,946 A * | 8/1962 | Hawk | B65D 90/54 |
| | | | 52/196 |
| 3,076,403 A * | 2/1963 | Behlen | A01F 25/16 |
| | | | 99/646 R |
| 3,418,069 A | 12/1968 | Eugene et al. | |
| 3,664,072 A * | 5/1972 | Lieckfeld | B65D 88/26 |
| | | | 52/63 |
| 3,712,002 A * | 1/1973 | Hillinger | B65D 88/26 |
| | | | 52/63 |
| 4,663,787 A | 5/1987 | Kolsch | |
| 4,877,964 A | 10/1989 | Tanaka et al. | |
| 4,896,042 A | 1/1990 | Humphreys | |
| 5,690,415 A | 11/1997 | Krehl | |
| 5,729,930 A * | 3/1998 | Schust | B60J 1/17 |
| | | | 49/372 |
| 5,744,094 A | 4/1998 | Castberg et al. | |
| 5,768,853 A | 6/1998 | Bushnell et al. | |
| 5,891,399 A | 4/1999 | Owesen | |
| 5,925,885 A | 7/1999 | Clark et al. | |
| 6,242,753 B1 | 6/2001 | Sakurai | |
| 6,398,970 B1 | 6/2002 | Justel et al. | |
| 6,402,774 B1 | 6/2002 | Caldironi | |
| 6,403,030 B1 | 6/2002 | Horton, III | |
| 6,447,720 B1 | 9/2002 | Horton, III et al. | |
| 6,539,727 B1 | 4/2003 | Burnett | |
| 6,566,659 B1 | 5/2003 | Clark et al. | |
| 6,576,190 B1 | 6/2003 | Park | |
| 6,607,170 B1 | 8/2003 | Hoftman | |
| 6,656,424 B1 | 12/2003 | Deal | |
| 6,774,382 B2 | 8/2004 | Yoshida | |
| 6,897,460 B2 | 5/2005 | Kobayashi et al. | |
| 6,911,177 B2 | 6/2005 | Deal | |
| 6,932,494 B1 | 8/2005 | Burnett et al. | |
| 7,175,806 B2 | 2/2007 | Deal et al. | |
| 7,282,728 B2 | 10/2007 | Culbert | |
| 7,317,393 B2 | 1/2008 | Maloney | |
| 7,329,026 B1 | 2/2008 | Hayman et al. | |
| 7,380,627 B2 | 6/2008 | Huang et al. | |
| 7,459,694 B2 | 12/2008 | Scheir et al. | |
| 7,540,998 B2 | 6/2009 | Terwilliger et al. | |
| 7,665,227 B2 | 2/2010 | Wright et al. | |
| 7,829,867 B2 | 11/2010 | Hlavinka et al. | |
| 7,875,247 B2 | 1/2011 | Clark et al. | |
| 8,193,515 B2 | 6/2012 | Kreitenberg | |
| 8,236,236 B2 | 8/2012 | Garner | |
| 8,563,059 B2 | 10/2013 | Luckhardt et al. | |
| 8,895,939 B2 | 2/2014 | Lyslo et al. | |
| 8,745,782 B2 | 6/2014 | Bernat | |
| 8,791,441 B1 | 7/2014 | Lichtblau | |
| 8,816,301 B2 | 8/2014 | Stibich et al. | |
| 8,872,669 B2 | 10/2014 | Stibich et al. | |
| 8,907,304 B2 | 12/2014 | Kreitenberg | |
| 9,165,756 B2 | 10/2015 | Stibich et al. | |
| 9,440,041 B1 * | 9/2016 | Lacayo | A61M 16/14 |
| 9,492,577 B1 | 11/2016 | Dayton | |
| 9,504,345 B2 | 11/2016 | Stibich et al. | |
| 9,517,284 B1 | 12/2016 | Stibich et al. | |
| 9,551,528 B2 | 1/2017 | Kong et al. | |
| 9,744,255 B2 | 8/2017 | Stibich et al. | |
| 9,867,894 B2 | 1/2018 | Stibich et al. | |
| 9,974,243 B2 * | 5/2018 | Martin | A01G 7/045 |
| 10,010,636 B2 | 7/2018 | Henniges et al. | |
| 10,154,549 B2 | 12/2018 | Nasu et al. | |
| 2002/0098139 A1 | 7/2002 | Sparks | |
| 2002/0133886 A1 | 9/2002 | Severns et al. | |
| 2002/0190073 A1 * | 12/2002 | Hewett | A47K 10/424 |
| | | | 221/46 |
| 2003/0048633 A1 | 3/2003 | Shiau et al. | |
| 2003/0086821 A1 | 5/2003 | Matthews | |
| 2003/0137834 A1 | 7/2003 | Jigamian et al. | |
| 2004/0030371 A1 * | 2/2004 | Barghelame | A61H 33/06 |
| | | | 607/96 |
| 2004/0050008 A1 | 3/2004 | Mintie | |
| 2004/0052702 A1 | 3/2004 | Shuman et al. | |
| 2004/0074212 A1 | 4/2004 | Yachi et al. | |
| 2004/0151617 A1 | 8/2004 | Zanakis et al. | |
| 2004/0175290 A1 | 9/2004 | Scheir et al. | |
| 2005/0058013 A1 | 3/2005 | Warf et al. | |
| 2005/0133740 A1 | 6/2005 | Gardner | |
| 2005/0163686 A1 | 7/2005 | Bettenhausen et al. | |
| 2006/0011397 A1 | 1/2006 | Huang et al. | |
| 2006/0159583 A1 | 7/2006 | Naslund et al. | |
| 2006/0261291 A1 | 11/2006 | Gardner | |
| 2006/0263275 A1 | 11/2006 | Lobach | |
| 2006/0284109 A1 | 12/2006 | Scheir et al. | |
| 2007/0108273 A1 | 5/2007 | Harper et al. | |
| 2007/0202005 A1 | 8/2007 | Maschke | |
| 2007/0255266 A1 | 11/2007 | Cumbie et al. | |
| 2007/0257205 A1 | 11/2007 | Rocha-Alvarez et al. | |
| 2008/0056933 A1 | 3/2008 | Moore et al. | |
| 2008/0253941 A1 | 10/2008 | Wichers et al. | |
| 2008/0260601 A1 | 10/2008 | Lyon | |
| 2009/0008420 A1 * | 1/2009 | Zimmermann | A45C 5/03 |
| | | | 224/282 |
| 2009/0217547 A1 | 9/2009 | Kim et al. | |
| 2009/0250407 A1 | 10/2009 | Delano | |
| 2009/0256034 A1 * | 10/2009 | Poyner | B01F 15/00733 |
| | | | 248/154 |
| 2009/0304553 A1 | 12/2009 | Gordon | |
| 2010/0183476 A1 | 7/2010 | Lu | |
| 2010/0247403 A1 | 9/2010 | Hancock | |
| 2010/0266445 A1 | 10/2010 | Campagna | |
| 2011/0054574 A1 | 3/2011 | Felix | |
| 2011/0073774 A1 | 3/2011 | Taylor et al. | |
| 2011/0215261 A1 | 9/2011 | Lyslo et al. | |
| 2011/0305597 A1 | 12/2011 | Farren | |
| 2012/0047763 A1 | 3/2012 | Abramovich et al. | |
| 2012/0056102 A1 | 3/2012 | Stanley et al. | |
| 2012/0093688 A1 | 4/2012 | Harmon et al. | |
| 2012/0305787 A1 | 12/2012 | Henson | |
| 2012/0313532 A1 | 12/2012 | Stibich et al. | |
| 2012/0315186 A1 | 12/2012 | Davis | |
| 2013/0078142 A1 | 3/2013 | Gordon | |

(56) References Cited

U.S. PATENT DOCUMENTS

| | | |
|---|---|---|
| 2013/0224086 A1 | 8/2013 | Stibich et al. |
| 2013/0272929 A1 | 10/2013 | Pelfrey et al. |
| 2013/0330235 A1 | 12/2013 | Stibich et al. |
| 2014/0060095 A1 | 3/2014 | Shur et al. |
| 2014/0148047 A1 | 5/2014 | Gaither |
| 2014/0158910 A1 | 6/2014 | Fletcher |
| 2014/0161663 A1 | 6/2014 | Farren et al. |
| 2014/0348701 A1 | 11/2014 | Kirschman |
| 2015/0025300 A1 | 1/2015 | Hill et al. |
| 2015/0209462 A1 | 7/2015 | Turbett et al. |
| 2015/0314026 A1 | 11/2015 | Mauzerall et al. |
| 2015/0359915 A1 | 12/2015 | Farren et al. |
| 2015/0367008 A1 | 12/2015 | Romo et al. |
| 2016/0023417 A1 | 1/2016 | Hanson et al. |
| 2016/0074546 A1 | 3/2016 | Rizzone |
| 2016/0340927 A1 | 11/2016 | Rizzotto |
| 2017/0051449 A1 | 2/2017 | Nam et al. |
| 2017/0216472 A1 | 3/2017 | Stibich et al. |
| 2017/0216473 A1 | 8/2017 | Rizzone |
| 2017/0224858 A1 | 8/2017 | Stibich et al. |
| 2017/0368213 A1 | 12/2017 | Mintie et al. |
| 2018/0007845 A1* | 1/2018 | Martin .................. A01G 7/045 |
| 2018/0207303 A1 | 7/2018 | Farren et al. |
| 2018/0339076 A1 | 11/2018 | Stibich et al. |
| 2019/0082619 A1* | 3/2019 | Martin .................. A01G 31/00 |

FOREIGN PATENT DOCUMENTS

| | | | | |
|---|---|---|---|---|
| CN | 2117167 | 9/1992 | | |
| CN | 2678651 | 2/2005 | | |
| CN | 201558350 | 8/2010 | | |
| CN | 101890174 | 11/2010 | | |
| CN | 201755324 | 3/2011 | | |
| CN | 203232241 | 10/2013 | | |
| CN | 204864168 | 12/2015 | | |
| EP | 0691444 A1 * | 1/1996 | ............... | E04H 7/28 |
| EP | 1588720 | 10/2005 | | |
| EP | 1778055 | 5/2007 | | |
| EP | 2537600 | 12/2012 | | |
| FR | 2378705 A1 * | 8/1978 | ............. | B65D 88/30 |
| FR | 2964217 A1 | 3/2012 | | |
| JP | S47-38719 B | 9/1972 | | |
| JP | S55-12959 U | 1/1980 | | |
| JP | H06-63108 | 3/1994 | | |
| JP | H07003649 | 1/1995 | | |
| JP | H09220275 | 8/1997 | | |
| JP | 2000245816 | 9/2000 | | |
| JP | 2006-057898 | 3/2006 | | |
| JP | 2008526466 | 7/2008 | | |
| JP | 2008229127 | 10/2008 | | |
| JP | 2009050584 | 3/2009 | | |
| JP | 2012075711 | 4/2012 | | |
| KR | 20130000038 | 1/2013 | | |
| KR | 20130131958 | 12/2013 | | |
| KR | 1020120052521 | 5/2015 | | |
| WO | 01/60419 | 8/2001 | | |
| WO | 02/058744 | 8/2002 | | |
| WO | 2003021632 | 3/2003 | | |
| WO | 2004011163 | 2/2004 | | |
| WO | 2005/082426 | 9/2005 | | |
| WO | 2007/008879 | 1/2007 | | |
| WO | 2007008879 | 1/2007 | | |
| WO | 2007/020282 | 2/2007 | | |
| WO | 2007102798 | 9/2007 | | |
| WO | 2007/089312 | 8/2009 | | |
| WO | 2009097389 | 8/2009 | | |
| WO | 2010/030039 | 3/2010 | | |
| WO | 2010/042849 | 4/2010 | | |
| WO | 2011088394 | 7/2011 | | |
| WO | 2012085250 | 6/2012 | | |
| WO | 2012/142427 | 10/2012 | | |
| WO | WO2012/142427 | 10/2012 | | |
| WO | 2014/022717 | 2/2014 | | |
| WO | 2014051906 | 4/2014 | | |
| WO | 2014/100493 | 6/2014 | | |
| WO | 2014088580 | 6/2014 | | |
| WO | 2015054389 | 4/2015 | | |
| WO | 2015116876 | 8/2015 | | |
| WO | 2016044759 | 3/2016 | | |
| WO | 2016073463 | 5/2016 | | |
| WO | 2017136812 | 10/2017 | | |
| WO | 2018005104 | 1/2018 | | |

OTHER PUBLICATIONS www.lumalier.com, DC Mail and Object Disinfection, retrieved from internet on May 15, 2015, 2 pages.
International Searching Authority, International Search Report and Written Opinion for PCT Patent Application No. US2017/046129 dated Nov. 6, 2017, 11 pages.
Patent Cooperation Treaty, International Preliminary Report on Patentability for International Application No. PCT/US2017/046129, dated Jun. 4, 2019, 6 pages.
Japanese Patent Office, Notice of the Reason for Refusal for Japanese Patent Application No. 2019-548863, dated Sep. 21, 2021, 8 pages.
European Patent Office, Office Action for European Patent Application No. 17 758 322.6, dated Dec. 17, 2019, 5 pages.
European Patent Office, Office Action for European Patent Application No. 17 758 322.6, dated Jun. 15, 2020, 5 pages.
European Patent Office, Office Action for European Patent Application No. 17 758 322.6, dated Nov. 25, 2020, 6 pages.
www.honeycando.com, Honey Can Do Storage Coset Installation Manual, dated 2011, 12 pages.
English Translation of Notice of The Reason For Refusal, Japanese Application No. 2019-548863, dated Jul. 19, 2022, 7 pgs.

* cited by examiner

SYSTEMS, CABINETS AND METHODS FOR DISINFECTING OBJECTS

CONTINUING DATA

The present application is a continuation-in-part from pending International Application No. PCT/US2017/016675 filed Feb. 6, 2017, which designates the United States and claims priority to U.S. application Ser. No. 15/363,917 filed Nov. 29, 2016 and U.S. Application No. 62/291,024 filed Feb. 4, 2016.

BACKGROUND OF THE INVENTION

1. Field of the Invention

This invention generally relates to the disinfection of objects and, more specifically to, systems, cabinets and methods for disinfecting objects.

2. Description of the Related Art

The following descriptions and examples are not admitted to be prior art by virtue of their inclusion within this section. In general, germicidal systems are designed to subject one or more surfaces and/or objects to a germicide to deactivate or kill microorganisms residing upon the surface/s and/or object/s. Applications of germicidal systems include but are not limited to sterilization, object disinfection, and room/area decontamination. Examples of area/room decontaminations system are those used in hospital rooms to disinfect the objects therein and those used in agricultural operations, such as those which are used to breed and/or farm animals. Examples of sterilizing systems are those used for sterilizing surgical tools, food or pharmaceutical packaging. A challenge in many applications is accessing all surfaces of an object to insure thorough disinfection of the object. In particular, some germicidal systems may only effectively treat surfaces which are facing the germicidal system and, thus, surfaces not facing the system may not be disinfected adequately.

Furthermore, surfaces of an object which are in contact with a surface of another object, such as the surface of an object touching the surface of a table or surfaces of a plurality of objects stacked upon each other are hidden from exposure and, thus, such surfaces are not disinfected. Objects which are particularly susceptible for being in contact with other objects are those which are relatively small and portable. Furthermore, such objects are often handled by humans, making them more likely to have germs on their surfaces. Some germicidal systems include trays for objects to be positioned on such that access to surfaces of the objects may be manipulated. Such trays, however, are labor and time intensive in that the objects must be carefully positioned to avoid overlapping the objects and, further, that the objects must be turned over during a disinfection process to insure disinfection of surfaces that were originally placed in contact with the trays.

A further challenge in many settings in which moveable equipment is used, such as in hospitals or agricultural operations, is for the moveable equipment to be adequately and consistently disinfected. For example, in hospitals, moveable equipment such as wheelchairs, mobile work stations, vital sign monitors and the like are frequently used and, thus, are highly prone to contamination by infectious microorganisms. Furthermore, such equipment is generally used in multiple locations in the hospital and, thus, tracking its use, its need for disinfection and/or insuring it has been disinfected in accordance with a set schedule can be a challenge. Moreover, the equipment faces the same challenges as mentioned above when disinfected by a germicidal system which effectively only treats surfaces facing the germicidal system.

Accordingly, it would be advantageous to develop devices and processes that can aid in disinfecting objects, particularly accessing all surfaces of objects during a disinfection process with minimal labor involved and minimal interruptions to the disinfection process.

SUMMARY OF THE INVENTION

Systems, cabinets and methods are provided for disinfecting objects. The following description of various embodiments of systems, cabinets and methods is not to be construed in any way as limiting the subject matter of the appended claims.

An embodiment of a system for disinfecting objects includes a disinfection apparatus and a cabinet. The disinfection apparatus includes a base supporting a germicidal source that extends out from the base. The base includes components operationally coupled to the germicidal source for operating the germicidal source and an air moving device configured to draw in air from an external ambient of the base. The disinfection apparatus is configured to route the air from the air moving device to the germicidal source. The cabinet includes a port and one or more air vents extending between an interior of the cabinet and an exterior of the cabinet. The port has a periphery that surrounds a portion of the disinfection apparatus such that when the disinfection apparatus is operating the air moving device draws in air from an external ambient of the cabinet and the drawn-in air and a germicide emitted from the germicidal source is projected into the cabinet.

An embodiment of a method for disinfecting one or more items includes positioning a disinfection apparatus in proximity to a cabinet, wherein the disinfection apparatus has a base supporting a germicidal source and the base includes components operationally coupled to the germicidal source for operating the germicidal source. The method further includes inserting the germicidal source into the cabinet such that at least a portion of the base is retained exterior to the cabinet and is operationally coupled to the germicidal source. Moreover, the method includes placing one or more items into the cabinet, closing the cabinet with the germicidal source and the one or more items in the cabinet and the base of the disinfection apparatus exterior to the cabinet, and then subsequently starting the disinfection source such that the germicidal source emits a germicide into the cabinet.

An embodiment of a cabinet includes a first port having a dimensionally adjustable periphery that is configured to conform to a periphery of an item partially inserted into the first port to seal the first port against the inserted item. The cabinet further includes a second port having a door and one or more air vents extending between an interior of the cabinet and an exterior of the cabinet.

BRIEF DESCRIPTION OF THE DRAWINGS

Other objects and advantages of the invention will become apparent upon reading the following detailed description and upon reference to the accompanying drawings in which.

Figure 1:
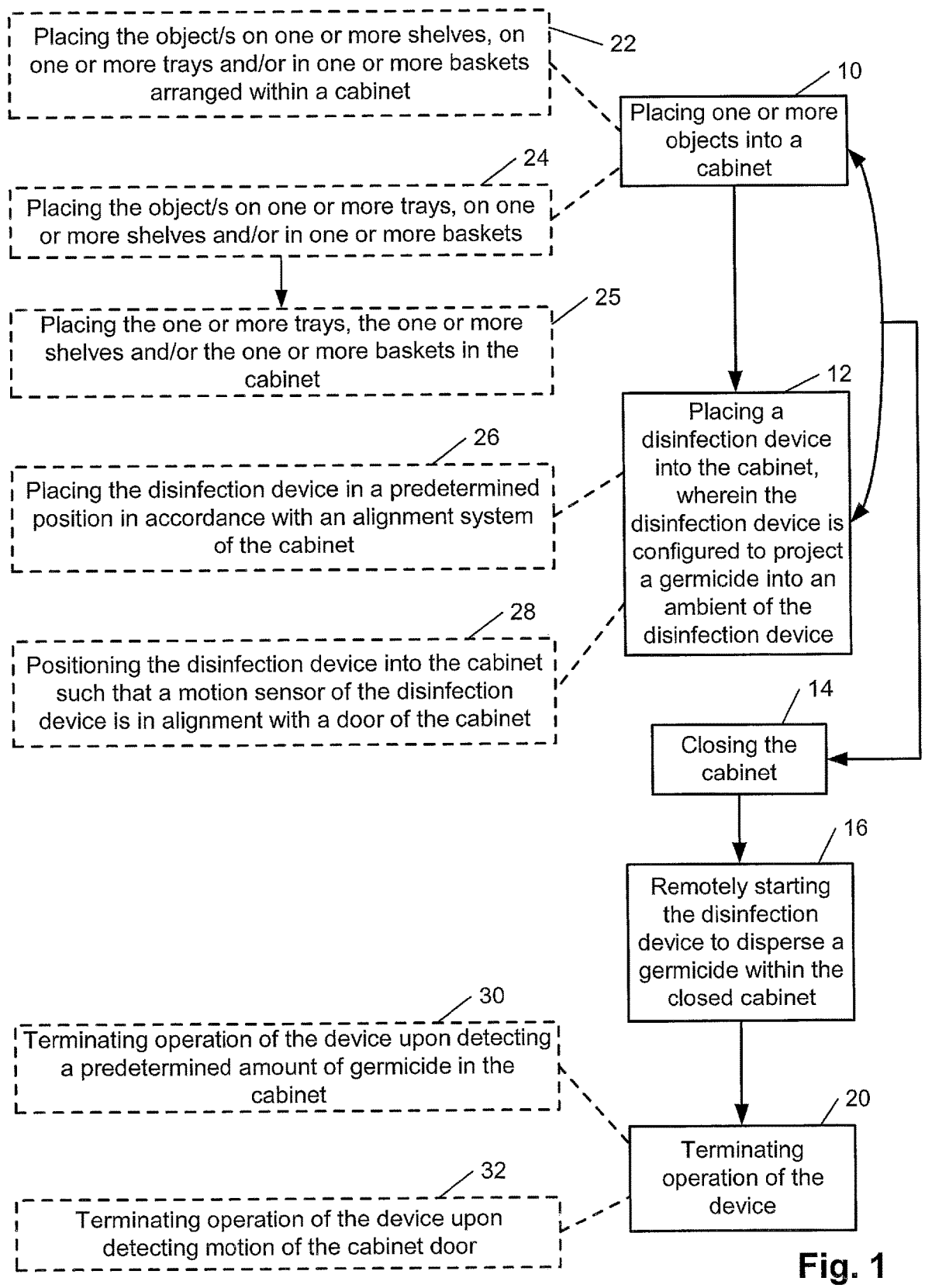
FIG. 1 illustrates an example flowchart of a method for disinfecting one or more objects in a cabinet.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Devices and methods are provided that increase the versatility of operationally independent disinfection apparatuses, allow a majority if not all exterior sides of an object to be simultaneously disinfected and offer a manner to determine if an object has been deemed suitable for a particular disinfection system. More specifically, methods are provided which include placing one or more objects into a cabinet, placing a disinfection device into the cabinet, closing the cabinet with the disinfection device and the one or more objects inside the cabinet and remotely starting the disinfection device to disperse a germicide within the closed cabinet as set forth in FIG. 1. In addition, a method is provided in FIG. 8 for disinfection of objects in a partitionable cabinet. Moreover, cabinets are provided which are specifically configured to enable such a processes as illustrated in FIGS. 3-7. Furthermore, support structures are provided which are configured to confirm an object placed thereon is suitable for a particular disinfection system, an example of which is set forth in FIGS. 9 and 10. Other examples of systems, cabinets and methods for disinfecting objects are provided in FIGS. 11-14 which enable a germicidal source to be inserted into a cabinet while retaining at least a portion of a base supporting the germicidal source exterior to the cabinet.

The objects considered for use in the methods, cabinets and support structures provided herein may include any configuration (i.e., shape, size, weight, material, construction, etc.) and may particularly depend on the configuration of the cabinet in which they are to be disinfected or the support structure upon which they are to be arranged for a disinfection process. In some cases, objects which are relatively small and portable may be suitable for some of the cabinets described herein. In particular, some of the cabinets described herein include support structures, such as trays, shelving and/or baskets to hold objects during a disinfection cycle. In such cases, objects occupying less than approximately 1.0 $ft^3$ and, in some cases, objects occupying less than approximately 0.5 $ft^3$ may be particularly applicable for such processes. In other cases, the cabinets described herein may be configured to disinfect larger objects, particularly those occupying more than approximately 1.0 $ft^3$ or even those occupying more than 5.0 $ft^3$. In any case, the methods, cabinets and support structures described herein may, in some cases, be used in hospitals. In such embodiments, objects which may be considered for use in the methods, cabinets and support structures provided herein may include medical items which are kept within a hospital, including medical equipment and supplies. Non-medical items may be considered for use in the methods, cabinets and support structures provided herein as well, such as but not limited to pens, pads of paper, pamphlets and television remote controls. In any case, objects of the same configuration or of different configurations may be considered for a given disinfection process.

Figure 11:
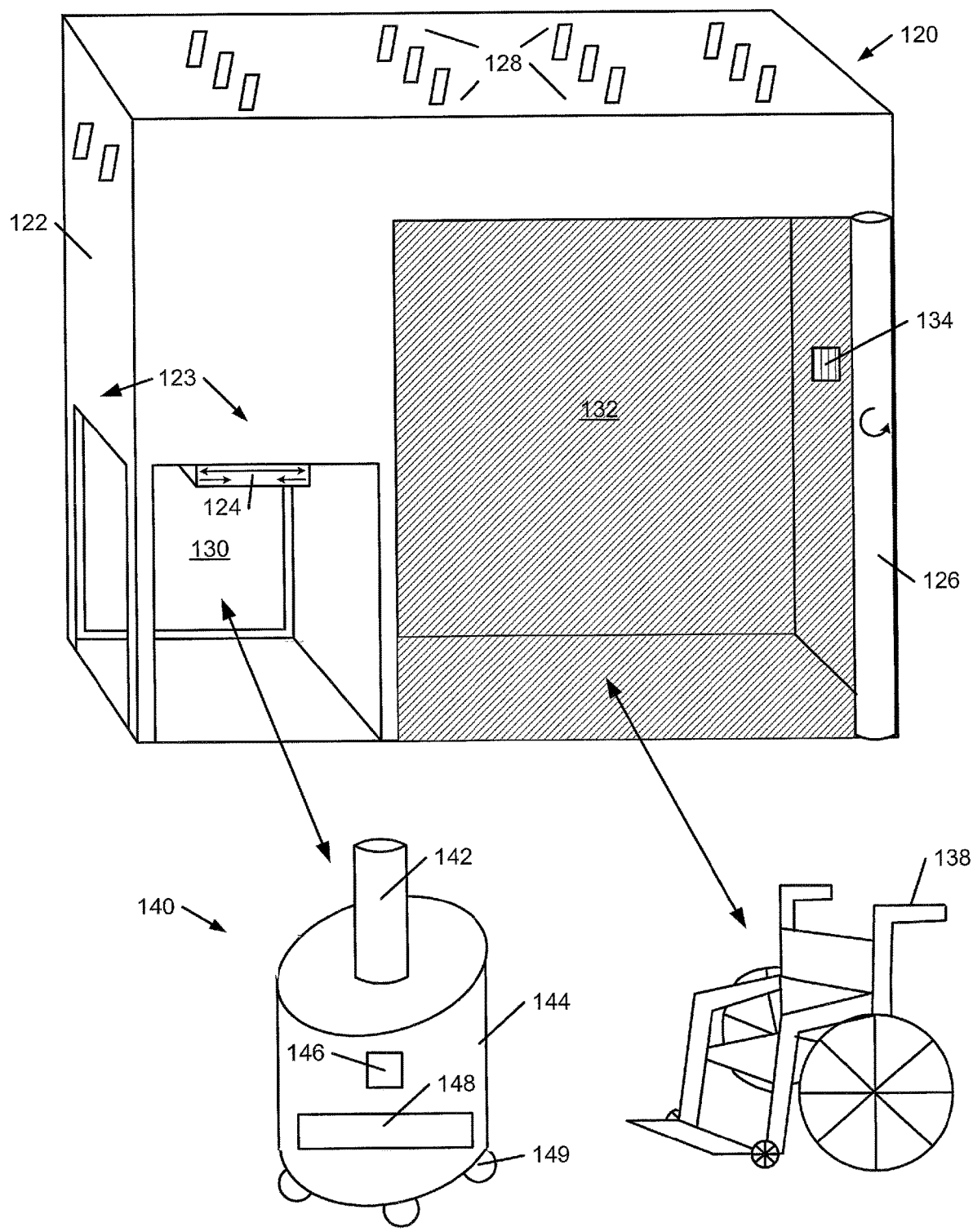
FIG. 11 illustrates a perspective view of another example cabinet for disinfecting one or more objects having a disinfection apparatus and a wheelchair disposed in proximity to the cabinet.
Figure 12:
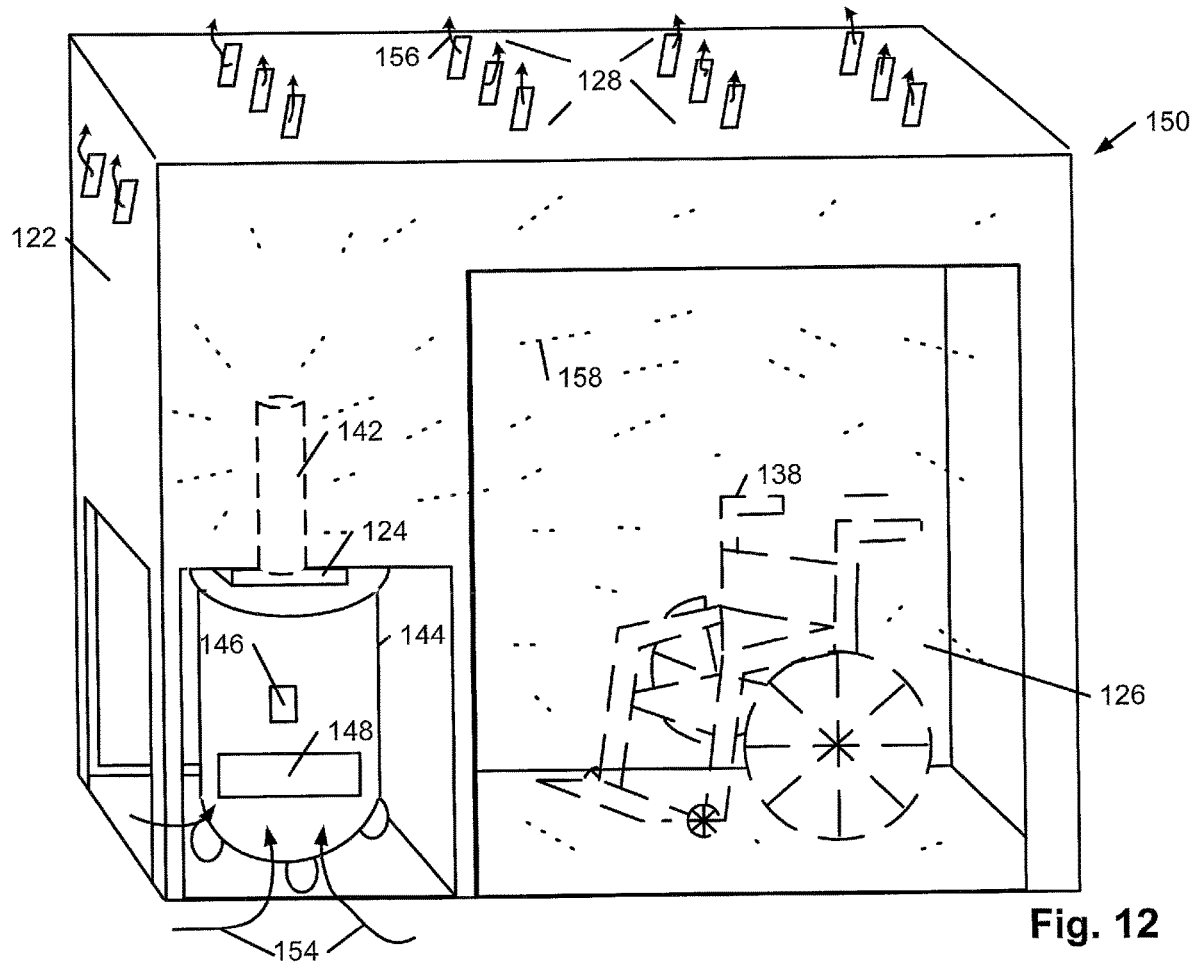
FIG. 12 illustrates a perspective view of a system for disinfecting one or more objects.
Figure 14:
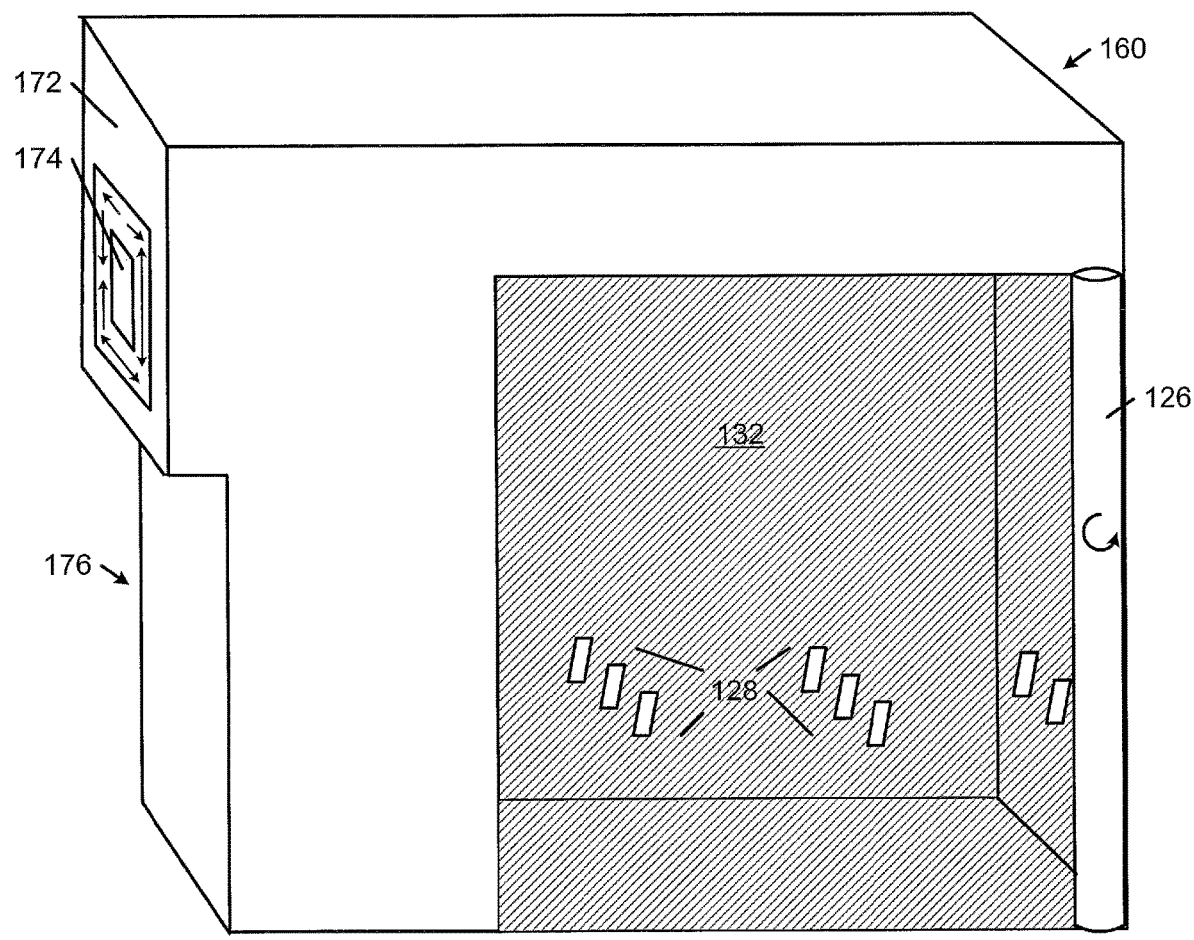
FIG. 14 illustrates a perspective view of another example cabinet for disinfecting one or more objects.

As noted above, FIG. 1 outlines a method for disinfecting one or more objects in a cabinet. As shown, block 10 includes placing one or more objects into a cabinet. In some cases, the step of placing the one or more objects into the cabinet may include placing the one or more objects onto a floor of the cabinet. In addition or alternatively, the step of placing the one or more objects into the cabinet may include wheeling the one or more objects into the cabinet. Either embodiment may be particularly suitable for placing a relatively large object into the cabinet particularly those occupying more than approximately 1.0 $ft^3$. Examples of relatively large objects may include but are not limited to medical equipment, wheeled over-the-bed tables, intravenous poles, and carts. Examples of a system and cabinets having configurations suitable for placing one or more objects onto a floor of a cabinet and/or wheeling object/s into a cabinet are shown in FIGS. 11, 12 and 14 and are described in more detail below.

In some additional or alternative cases, the step of placing the one or more objects into the cabinet of FIG. 1 may include placing one or more of the object/s on one or more shelves arranged in the cabinet, placing one or more of the object/s on one or more trays arranged in the cabinet and/or placing one or more of the object/s in one or more baskets arranged within a cabinet as set forth in block 22. In some embodiments, the step of placing the one or more objects into the cabinet may additionally or alternatively include placing the one or more objects on one or more trays, on one or more shelves and/or in one or more baskets and then placing the one or more trays, the one or more shelves and/or the one or more baskets in the cabinet as respectively set forth in blocks 24 and 25. In any case, the shelving, basket/s and/or tray/s may be arranged at any location in the cabinet. In some embodiments, one or more shelves, one or more baskets and/or one or more trays may be attached and/or extend from sidewalls of the cabinet and/or door/s of the cabinet. In addition or alternatively, one or more baskets, one or more shelves and/or one or more trays may be hung from the ceiling of the cabinet. Furthermore, one or more baskets and/or one or more trays may be arranged on a floor of the cabinet and/or may be arranged on a shelf in the cabinet.

In any case, the shelving, the basket/s and/or the tray/s considered for the methods, cabinets and support structures provided herein include portions which are transparent to germicidal light and/or include through holes. In some embodiments, the size of the through holes in the shelving, basket/s and/or tray/s may be large relative to the framework surrounding the through holes (i.e., the through holes may occupy more space than the framework surrounding the through holes, such as commonly found in wired racks or polymer frameworks having a configuration similar to a wire rack). In some cases, the framework surrounding the through holes may be partially or entirely made of materials transparent to germicidal light. In some embodiments, regardless of whether the shelving, basket/s and/or tray/s include through holes, one or more of the shelves, basket/s and/or tray/s may be made of entirely material/s transparent to germicidal light. An example of a material transparent to germicidal light is quartz, but other materials may be considered.

In some cases, the shelving, basket/s and/or trays may include one or more suspension nubbles for objects to be placed on and such that they may be suspended above the attached shelving, basket or tray. The suspension nubble/s may allow a greater surface area of object/s to be exposed to germicide that is projected from a disinfection device arranged in the cabinet and, thus, may increase the efficacy of disinfecting the object/s during a disinfection process. In some cases, the suspension nubble/s may comprise a material which is transparent to germicidal light, particularly for embodiments in which a disinfection device to be used in the cabinet comprising the shelving, basket or tray has a germicidal light source. In some of such embodiments, the other portions of the shelving, basket or tray comprising the one or more suspension nubbles may not be transparent to germicidal light or include through holes. In particular, in some cases, the only portion of a shelf, basket or tray made of a material transparent to germicidal light may be the one or more suspension nubbles. In other cases, however, the other portions of the shelving, basket or tray comprising the one or more suspension nubbles may include a material transparent to germicidal light or include through holes. In alternative embodiments, the suspension nubble/s may not be transparent to germicidal light.

Figure 2:
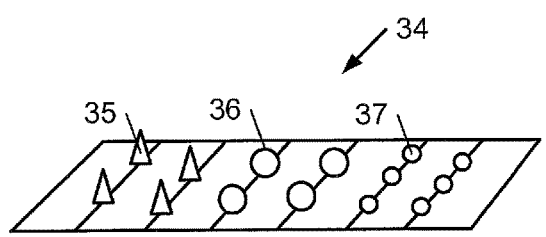
FIG. 2 illustrates a perspective view of an example shelf having nubbles for suspending objects thereon.

An example shelf 34 is illustrated in FIG. 2 having a variety of nubbles. In particular, FIG. 2 shows shelf 34 with a wire rack having suspension nubbles 35, 36 and 37 attached to bars of the rack. As shown, suspension nubbles 35 are conical, which may be advantageous for minimizing the amount of contact with an object placed thereon. An alternative shape for suspension nubbles may be spherical, as shown by nubbles 36 in FIG. 2. Several other shapes may be considered as well, such as but not limited to pyramids and triangular prisms. Another type of suspension nubble configuration that may be considered for the shelving, basket/s and/or tray/s for the cabinets and methods described herein may be a suspension nubble having a substantially flat upper surface by which to receive an object. For example, circular wafers, such as shown by suspension nubbles 37 in FIG. 2, or any other shaped wafers may be used. Alternatively, square or rectangular blocks or inverted cones or prisms may be used. In any of such cases, the substantially flat upper surface of a suspension nubble may, in some embodiments, may be roughed to aid in retaining an object thereon. In other cases, however, the substantially flat upper surface of a suspension nubble may be smooth.

Regardless of their shape, nubble/s may, in some cases, have a height of at least approximately 2 cm. In other embodiments, suspension nubble/s may have a height of less than approximately 2 cm. In some cases, all suspension nubbles on a shelf, basket and/or tray may have the same height. Such a configuration may aid in stabilizing an object that spans more than one of the suspension nubbles for support. In other embodiments, the height of some or all suspension nubbles on a shelf, basket and/or tray may be different. Furthermore, in some cases, a shelf, basket and/or tray may have suspension nubbles of the same configuration (i.e., the same shape and/or size). In other embodiments, the size and/or shape of some or all suspension nubbles on a shelf, basket and/or tray may be different.

In any case, suspension nubble/s may, in some embodiments, be affixed to a shelf, basket and/or tray such that they are not readily removable from or moveable along the shelf, basket and/or tray. In yet other cases, suspension nubble/s may be attached in a manner such that they do not move along the shelf, basket and/or tray to which they are attached, but yet may be removed from the shelf, basket and/or tray by human force. In this manner, the suspension nubble/s may be adjusted for different objects and/or different disinfection cycles. In other embodiments, suspension nubble/s may be configured to move (e.g., slide) along the shelf, basket and/or tray to which they are attached. In any case, suspension nubbles may include any attachment or mounting means for coupling to a shelf, basket and/or tray. In some embodiments, a suspension nubble may include one or more lower members that are configured to attach to a particular surface configuration. For example, in cases in which a suspension nubble is attached to a wired rack, the suspension nubble may include one or more lower members dimensionally and collectively configured to securely conform to a bar of the wired rack. Although FIG. 2 shows suspension nubbles attached to a bars of a wire rack, the use of nubbles are not necessarily so restricted. In particular, suspension nubbles may be attached to any surface of shelf, basket and/or tray of any configuration.

In any case, in some embodiments, the upper portion of suspension nubble/s may include a different material than their attachment/mounting means. For example, in some cases, the upper portion of a suspension nubble may include a material that is transparent to germicidal light, such as quartz for instance, to allow a greater surface area of an object arranged thereon to be exposed to germicidal light during a disinfection cycle. The attachment/mounting means of the nubble, however, may include a different material and, in particular embodiments, may include a material which is not transparent to germicidal light. A variance in materials between the upper portion of a suspension nubble and its attachment/mounting means may be particularly applicable for embodiments in which the material used for the upper portion of the suspension nubble is not conducive for coupling to the material of the shelving, basket/s or tray/s. Alternatively, the upper portion of suspension nubble/s and their attachment/mounting means may be made of the same material/s and, in particular embodiments, may be in the form of a single composite material.

The term "cabinet" as used herein refers to an article for enclosing and holding one or more items, wherein the article has a door for receiving the one or more items and for closing the cabinet, and wherein the article may be either moved wholly or moved by dismantling at least some of the framework of the cabinet and reconstructing the cabinet from the dismantled framework at a different location. The term is distinct from areas of a building that are primarily bordered by fixed constructs of a building, such as by drywall or concrete, in that those constructs cannot be dismantled and readily reused to construct a wall. In particular, the term "cabinet" as used herein does not refer to rooms in a building, hallways, bathrooms, or closets having fixed sidewalls composed of materials commonly used to define interior spaces within a building such as but not limited to drywall or concrete. In contrast, the term is inclusive to reconstructable and/or moveable articles. For example, the term is inclusive to wall mounted articles, including but not limited to backless boxes which utilize a wall of a room to form an enclosure for the cabinet. In particular, wall mounted cabinets may be either moved wholly or moved by dismantling the cabinet and reconstructing the cabinet from the dismantled framework at a different location. Furthermore, the term "cabinet" as used herein encompasses free-standing reconstructable or moveable enclosures. Moreover, the term encompasses reconstructable or moveable articles which utilize the floor and/or the ceiling to form the enclosure for the cabinet. As such, articles which do not include a floor and/or a ceiling but which form an enclosure with a floor or ceiling of a building may be considered herein a cabinet when the article is arranged in such a manner.

As shown in block 12, the method outlined in FIG. 1 further includes placing a disinfection device into the cabinet. The doubled arrow line between blocks 10 and 12 indicates that either process may be conducted prior to the other or they may be performed at substantially the same time. In any case, the method continues to block 14 to close the cabinet and further to block 16 to remotely start the disinfection device to disperse a germicide within the closed cabinet. In particular, a user interface remote to the disinfection apparatus and wirelessly coupled to the disinfection apparatus to start operation thereof may be activated by a user outside of the cabinet.

In some cases, the disinfection device may be configured to be independently operational from the cabinet. Alternatively stated, the disinfection device placed into the cabinet may be configured to be operational independent from the cabinet. More specifically, the disinfection devices considered herein may be free-standing devices having their own power source and/or a power cord for accessing their own power. Thus, the functional features of the disinfection device need not be coupled to the cabinet for the disinfection device to operate. Such a configuration of a disinfection device does not necessarily mandate that the disinfection device be operationally independent from the cabinet during a disinfection cycle, but rather that it merely has the configuration to do so. For instance, as set forth in more detail below, the cabinets described herein may, in some embodiments, include a power outlet arranged along an interior surface for receiving a power plug and further a power cord coupled to the power outlet and extending out from an exterior surface of the cabinet. Such a configuration may be useful for supplying power to the disinfection device through the cabinet. In particular, a power plug of a disinfection device may be plugged into the power outlet of the cabinet and the power cord of the cabinet may be plugged into a power outlet coupled to a mains power supply of a building. In this manner, the power cord of the disinfection device need not be routed exterior to the cabinet. In other embodiments, however, the power cord of the disinfection device may be routed exterior to the cabinet, such as under a sidewall of the cabinet or through a hole along a sidewall of the cabinet, to directly connect the disinfection device to a power outlet coupled to a mains power supply of a building.

In any case, the method outlined in FIG. 1 includes terminating operation of the disinfection device as denoted in block 20 and subsequently removing one or more of the object/s and/or the disinfection device. In some embodiments, operation of the disinfection device may be terminated upon receiving a signal from a remote user interface of the device. In this manner, the timing of the termination may be selected by an individual. In other cases, operation of the disinfection device may be automatically terminated after a predetermined amount of time (which may be a time preset by an individual setting up a particular disinfection cycle in the cabinet or may be a default time preset for disinfection cycles conducted in the cabinet). In yet other embodiments, operation of the disinfection device may be automatically terminated after a predetermined amount of germicide is detected in the cabinet as denoted in block 30 in FIG. 1 and described in more detail below. In general, a disinfection device may include program instructions to terminate its operation based on any one or more of such bases for termination. In some cases, a disinfection device may further include program instructions to terminate its operation upon detecting motion of a door comprising the cabinet as denoted in block 32 in FIG. 1 and described in more detail below.

The disinfection devices considered herein may be any device configured to generate a dispersible germicide. In particular, the disinfection devices considered herein may be any device or apparatus configured to generate a germicide in form of a liquid, a vapor, a gas, a plasma or germicidal light. In some cases, a disinfection device may be configured to generate more than one type of germicide. As used herein, the term "germicide" refers to an agent for deactivating or killing microorganisms, particularly disease carrying and/or disease producing microorganisms (a.k.a, germs). The term "kill," as used herein, means to cause the death of an organism. In contrast, the term "deactivate," as used herein, means to render an organism unable to reproduce without killing. As such, a germicide which is configured to deactivate a microorganism, as used herein, refers to an agent which renders a microorganism unable to reproduce but leaves the organism alive. Furthermore, the term "disinfection device" as used herein refers to a collection of one or more components used to generate and disperse a germicide. In some embodiments, a disinfection device may include components in addition to the component/s used to generate the germicide to effect the dispersal of the germicide from the generation component/s. In any case, the disinfection devices described herein may include any number of germicidal sources, depending on the design specifications of the disinfection device.

In some cases, a germicidal source of the disinfection devices described herein may be configured to generate a liquid, vapor, gaseous or plasma germicide that is molecularly configured to deactivate and/or kill microorganisms. As used herein, the phrase "molecularly configured" refers to the elemental composition of a substance (i.e., the number and type of atoms making up a substance) to impart the function stated after the phrase. In some embodiments, the functionality of a liquid, vapor, gaseous or plasma germicide to deactivate and/or kill a microorganism may be attributed to the elements constituting the germicide and, thus, such germicides may be referenced as being molecularly configured to deactivate and/or kill microorganisms. This is in contrast to liquid, vapor, gaseous or plasma germicides which impart their deactivation and/or killing functionality by the manner in which they are used. For example, boiling water and steam are often effective sterilizing agents due to the temperature at which they are employed rather than their molecular composition. An example of a gaseous germicide which deactivates or kills microorganisms by the manner in which it is used is air at a very high temperature. Furthermore, the germicidal effectiveness of some plasma germicides is primarily due to the presence and activity of charged particles making up the plasma rather than the molecular composition of the charged particles.

An example of a gaseous germicide that is molecularly configured to kill microorganisms is ozone. Examples of plasmas germicides that are molecularly configured to deactivate or kill microorganisms are those that employ or generate reactive oxygen species. Examples of liquid and vapor germicides that are molecularly configured to deactivate or kill microorganisms include liquid and vapor disinfection solutions having a principle disinfection agent such as but not limited to bleach, hydrogen peroxide, chlorine, alcohol, quaternary ammonium compounds or ozone. In any of such cases, the liquid and vapor germicides may be aqueous or non-aqueous. It is noted that although germicidal sources which are configured to generate a liquid, vapor, gaseous or plasma germicide that is molecularly configured to deactivate or kill microorganisms are discussed in detail above, the disinfection devices considered herein may, in some embodiments, include a germicidal source configured to generate a liquid, vapor, gaseous or plasma germicide which imparts its deactivation or killing functionality by the manner in which it is used, such as via boiling water, steam or heated air. In any case, examples of disinfection devices which may be configured to disperse liquid, vapor, gaseous, or plasma germicides include but are not necessarily limited to liquid sprayers, foggers, plasmas torchers and misting systems including wet and dry mist systems. As used herein, the term "mist" refers to a suspension of minute globules of a liquid in a gas. For use herein, a germicidal mist is categorized as a liquid germicide.

As noted above, a germicidal source of the disinfection devices described herein may, in some embodiments, be a source configured to generate germicidal light. The term "germicidal light" refers to light which is capable of deactivating or killing microorganisms, particularly disease carrying and/or disease producing microorganisms (a.k.a., germs). Ranges of light which are known to be germicidal include ultraviolet light between approximately 200 nm and approximately 320 nm, particularly 220 nm and between 260 nm and 265 nm, and visible violet-blue light (also known as high-intensity narrow-spectrum (HINS) light) between approximately 400 nm and approximately 470 nm, particularly 405 nm. In some embodiments, a germicidal light source may generate ranges of light which are not germicidal such as but not limited to visible light greater than approximately 500 nm, but such capability will not deter from the reference of the light sources being germicidal. Furthermore, a light source or lamp may, in some cases, be characterized in the type of light it generates, but such characterization need not limit the light source or lamp to generating only that type of light. For example, an ultraviolet lamp is one which generates ultraviolet light but it may produce light of other wavelengths. In any case, the germicidal light sources considered for the disinfection devices described herein may be of any size and shape, depending on the design specifications of the disinfection devices. The terms "germicidal light source" and "germicidal lamp" are used interchangeably herein and refer to a collection of one or more components used to generate and disperse germicidal light.

Examples of germicidal light sources which may be configured to generate ultraviolet light and/or HINS light include discharge lamps, light emitting diode (LED) solid state devices, and excimer lasers. HINS lamps are generally constructed of LEDs. A discharge lamp as used herein refers to a lamp that generates light by means of an internal electrical discharge between electrodes in a gas. The term encompasses gas-discharge lamps, which generate light by sending an electrical discharge through an ionized gas (i.e., a plasma). The term also encompasses surface-discharge lamps, which generate light by sending an electrical discharge along a surface of a dielectric substrate in the presence of a gas, producing a plasma along the substrate's surface. As such, the discharge lamps which may be considered for the germicidal sources described herein include gas-discharge lamps as well as surface-discharge lamps. Discharge lamps may be further characterized by the type of gas/es employed and the pressure at which they are operated. The discharge lamps which may be considered for the germicidal sources described herein may include those of low pressure, medium pressure and high intensity. In addition, the gas/es employed may include helium, neon, argon, krypton, xenon, nitrogen, oxygen, hydrogen, water vapor, carbon dioxide, mercury vapor, sodium vapor and any combination thereof. In some embodiments, various additives and/or other substances may be included in the gas/es. In any case, the discharge lamps considered for the germicidal sources described herein may include those which generate continuous light and those which generate light in short durations, the latter of which are often referred to as flashtubes or flashlamps. Flashtubes or flashlamps that are used to supply recurrent pulses of light are often referred to as pulsed light sources.

A commonly used gas-discharge lamp used to produce continuous light is a mercury-vapor lamp, which may be considered for some of the disinfection devices described herein. It emits a strong peak of light at 253.7 nm, which is considered particularly applicable for germicidal disinfection and, thus, is commonly referenced for ultraviolet germicidal irradiation (UVGI). A commonly used flashlamp which may be considered for the disinfection devices described herein is a xenon flashtube. In contrast to a mercury-vapor lamp, a xenon flashtube generates a broad spectrum of light from ultraviolet to infrared and, thus, provides ultraviolet light in the entire spectrum known to the germicidal (i.e., between approximately 200 nm and approximately 320 nm). In addition, a xenon flashtube can provide relatively sufficient intensity in the spectrum which is known to be optimally germicidal (i.e., between approximately 260 nm and approximately 265 nm). Moreover, a xenon flashtube generates an extreme amount of heat, which can further contribute to the deactivation and killing of microorganisms.

Although they are not readily available on the commercial market to date, a surface-discharge lamp may be considered for some of the disinfection devices described herein as noted above. Similar to a xenon flashtube, a surface-discharge lamp produces ultraviolet light in the entire spectrum known to the germicidal (i.e., between approximately 200 nm and approximately 320 nm). In contrast, however, surface-discharge lamps operate at higher energy levels per pulse and, thus, greater UV efficiency, as well as offer longer lamp life as compared to xenon flashtubes. It is noted that the aforementioned descriptions and comparisons of a mercury-vapor lamp, a xenon flashlamp, and a surface discharge lamp in no way restrict the disinfection devices described herein to include such lamps. Rather, the aforementioned descriptions and comparisons are merely provided to offer factors which one skilled in the art may contemplate when selecting a germicidal light source for disinfection devices described herein.

As noted above, in some cases, the germicidal light source may be an excimer laser and, thus, the germicidal light used to disinfect objects in the cabinet may be a narrow beam of light. In such cases, a disinfection device comprising the laser may be configured to move the laser such that multiple or all locations in the cabinet are disinfected. Alternatively, a disinfection device may be configured to distribute germicidal light into an ambient of a room in a spacious manner such that at least the portions of an object in the vicinity of the disinfection device may be simultaneously disinfected. The disinfection device may be of any shape, size, or configuration in which to achieve such an objective.

In some cases, it may be advantageous for the methods and cabinets described herein to utilize a room disinfection device. More specifically, the methods and cabinets described herein may, in some cases, utilize disinfection devices with configurations to facilitate room disinfection. As used herein, the term "room disinfection device" refers to a device configured to disinfect a space which is suitable for human occupancy so as to deactivate, destroy or prevent the growth of disease-carrying microorganisms in the area. The phrase "a space which is suitable for human occupancy" as used herein refers to a space in which an adult human being of average size may comfortably occupy for at least a period of time to eat, sleep, work, lounge, partake in an activity, or complete a task therein. In some cases, spaces suitable for human occupancy may be bounded and include a door for entering and exiting the room. In other cases, a space suitable for human occupancy may be an area with indeterminate boundaries. Examples of spaces which are suitable for human occupancy include but are not limited to single patient rooms, multiple occupancy patient rooms, bathrooms, walk-in closets, hallways, bedrooms, offices, operating rooms, patient examination rooms, waiting and/or lounging areas and nursing stations. Although some disinfection devices used for the systems and methods described herein may be configured for room disinfection, the systems and methods need not be so limited. As such, a disinfection device used in the systems and methods described herein need not include all or any of the features described below that are generally associated with room disinfection devices.

In general, a room disinfection device includes configurations to distribute an effective amount of germicide in a spacious manner to an ambient of a room in which the device is arranged to maximize the number of surfaces and objects disinfected in the room. The device may be of any shape, size, or configuration in which to achieve such an objective. An example configuration of a room disinfection device which may be particularly considered for the disinfection devices discussed herein is for the germicidal source to be arranged within the device to distribute a germicide approximately 360° around the source. In such cases, the room disinfection device may be void of a component sufficient to block the germicide approximately 360° around the device such that germicide emitted from the germicidal source substantially encircles the device. Another configuration of a room disinfection device is to be automated to move through a room or area while the germicidal source is projecting germicide into an ambient of the room or area. For instance, some room disinfection devices include motorized wheels and processor-executable program instructions for activating the motorized wheels in accordance with a predetermined route and/or in response to sensors to maneuver around obstacles in the room or area while the germicidal source is emitting germicide/s. It is noted that although a room disinfection device may include such a configuration, such a movement feature would not be used in conjunction with the methods and cabinets disclosed herein.

Another common feature of room disinfection devices which may be optionally included in the disinfection devices considered for the methods described herein is to be configured to direct germicidal light to a region approximately 2 feet and approximately 4 feet from a floor of a room in which the apparatus is arranged. In particular, the region between approximately 2 feet and approximately 4 feet from a floor of a room is considered a "high touch" region of a room since objects of frequent use are generally placed in such a region. Examples of configurations which offer such light direction are disclosed in U.S. patent application Ser. No. 13/706,926 filed Dec. 6, 2012 and Ser. No. 13/708,208 filed Dec. 7, 2012 and International Patent Application No. PCT/US2014/059698 filed Oct. 8, 2014, all of which are incorporated herein by reference as if set forth fully herein. Other features specific to room disinfection devices are disclosed in such documents as well. For example, other features of room disinfection devices include wheels and/or a handle to affect portability for the devices. In addition, many room disinfection devices include configurations for remotely starting the devices such that individuals need not be present in the room when operation of the device commences.

Another feature of a room disinfection device which may be included in the disinfection devices considered for the methods described herein is to include configurations to distribute an effective amount of germicide to achieve at least a 2-log reduction in bacterial contamination on surfaces within a room or area that are greater than 1 meter or even 2 or 3 meters from the germicidal source. Configurations used to generate such an effect generally depend on the configuration of the germicidal source, particularly the size of the germicidal source, the intensity and/or frequency at which the germicide is dispersed and the orientation of the germicidal source in the apparatus. In general, the germicidal sources considered herein may, in some embodiments, be any shape, size, orientation or configuration and may be conducted at parameters to achieve a desired reduction in bacterial contamination on surfaces within a room or area that are greater than 1 meter or even 2 or 3 meters from the apparatus. An example of an orientation of a germicidal source which may aid in achieving such an effect is that the germicidal source may be vertically arranged (e.g., the germicidal source may be arranged lengthwise substantially perpendicular to a horizontal plane of the support structure) to aid in distributing the germicide greater distances within a room or area. Moreover, power fluxes of at least 1.0 W/m$^2$ may be generally used to achieve at least a 2-log reduction in bacterial contamination on surfaces within a room or area that are greater than 1 meter from the germicidal source.

In some cases, room disinfection devices may utilize configurations of other components in the device (i.e., other than the configurations of the germicidal source) to aid in achieving a desired reduction in bacterial contamination on surfaces within a room or area that are greater than 1 meter or even 2 or 3 meters from the germicidal source. For example, room disinfection devices may, in some embodiments, include an actuator coupled to the germicidal source and processor-executable program instructions for activating the actuator to move the germicidal source while the germicidal source is projecting germicide into an ambient of a room or area to aid in the distribution of germicide in a room or area. More specifically, the germicidal source may be moved in vertical, horizontal and/or diagonal directions via the actuator while the germicidal source is projecting germicide into an ambient of a room or area. Such a configuration may, in some embodiments, be included in the disinfection devices considered for the methods described herein and activated during a disinfection cycle in a cabinet. In particular, moving the germicidal source within a cabinet may aid in distributing the germicide among the different support structures in the cabinet.

Another component which is often included in room disinfection devices which may be included in the disinfection devices considered for the methods described herein is a movement detection sensor and/or a room/area occupancy sensor, such as a motion sensor, a thermal sensor, a Doppler sensor, or a photo recognition sensor. In particular, to prevent inadvertent exposure of a germicide to individuals during disinfection of a room or an area, the disinfection devices considered herein may include program instructions to inhibit or terminate activation of a power supply circuit to the germicidal source upon detecting movement and/or occupancy in the area/room in which the apparatus is arranged. In some cases, in order to use such disinfection devices in cabinets in which objects arranged therein are moved during a disinfection process (as described in more detail below), the disinfection devices may include a switch to activate and deactivate the movement detection or occupancy sensor comprising the device.

In other embodiments, the movement detection or occupancy sensor/s and associated program instructions of a disinfection device may be used when the disinfection device is placed in a cabinet for disinfecting objects. In particular, the method disclosed herein may include positioning the room disinfection device in the cabinet such that a movement sensor comprising the room disinfection device is in alignment with a door of the cabinet as set forth in block 28 of FIG. 1. In this manner, if the door to the cabinet is opened during operation of the disinfection device, power supply to the disinfection device will be terminated as set forth in block 32 of FIG. 1. In some of such embodiments, the cabinet may be void of mechanism/s to move objects therein. In other cases, the detection range of the movement sensor may be such that it is limited to the vicinity of the cabinet door and, thus, objects may be moved within the cabinet without detection of the sensor. Alternatively, the cabinets described herein may have a switch to activate and deactivate the mechanism/s used to move objects arranged therein such that it may be used in conjunction with a disinfection device having an active movement sensor.

In yet other embodiments, the cabinets disclosed herein may include an alternative safety mechanism/system to ensure door/s of the cabinet are closed when a disinfection device therein is projecting a germicide (i.e., a safety mechanism/system that does not include use of a movement sensor or an occupancy sensor comprising the disinfection device). For example, the cabinet may include a latch sensor on a door, which sends a signal to terminate operation of a disinfection apparatus when the door latch is opened. Alternatively, the cabinet may include a lock on a door and a germicidal sensor configured to prevent the inactivation of the lock when sensing a predetermined amount of germicide in the cabinet. Other safety mechanism/system ensuring door/s of the cabinet are closed when a disinfection device therein is projecting a germicide may be considered.

In any case, cabinets are provided herein which are specifically configured to enable simultaneous disinfection of a majority if not all surfaces of one or more objects disposed therein. As described in detail above, the cabinets include shelving, one or more baskets and/or one or more trays, at least portions of which are transparent to germicidal light and/or comprise through-holes. As further described above, the shelving, basket/s and/or tray/s may be arranged along the sidewalls, door/s, ceiling or floor of the cabinet. In addition to such support structures (i.e., shelving, basket/s and/or tray/s), the cabinets include a void of sufficient size to accommodate a disinfection device. In general, disinfection devices come in various sizes and, thus, the size of the void may vary, depending on the design of the cabinet. Some disinfection devices, particularly room disinfection devices, are relatively large units (i.e., 10 ft$^3$ or greater) and, thus, the void may, in some cases, be of sufficient size to accommodate such a device. In any case, the shelving, basket/s and/or tray/s of the cabinet are adjacent to the void and, in some cases, circumvent the void. In some embodiments, the void may centered in the cabinet, but in other embodiments the void may not be centered in the cabinet. In any case, portions of the support structures facing the void may be transparent to germicidal light and/or may include through-holes such that objects placed on the support structures may be exposed to a germicide projected from a disinfection device occupying the void. In some embodiments, the cabinet and/or the one or more support structures may include an automated means for moving one or more objects placed on or in the one or more support structures, such as a vibrator for example. For example, the cabinet may include vibrating wire racks.

Figure 3:
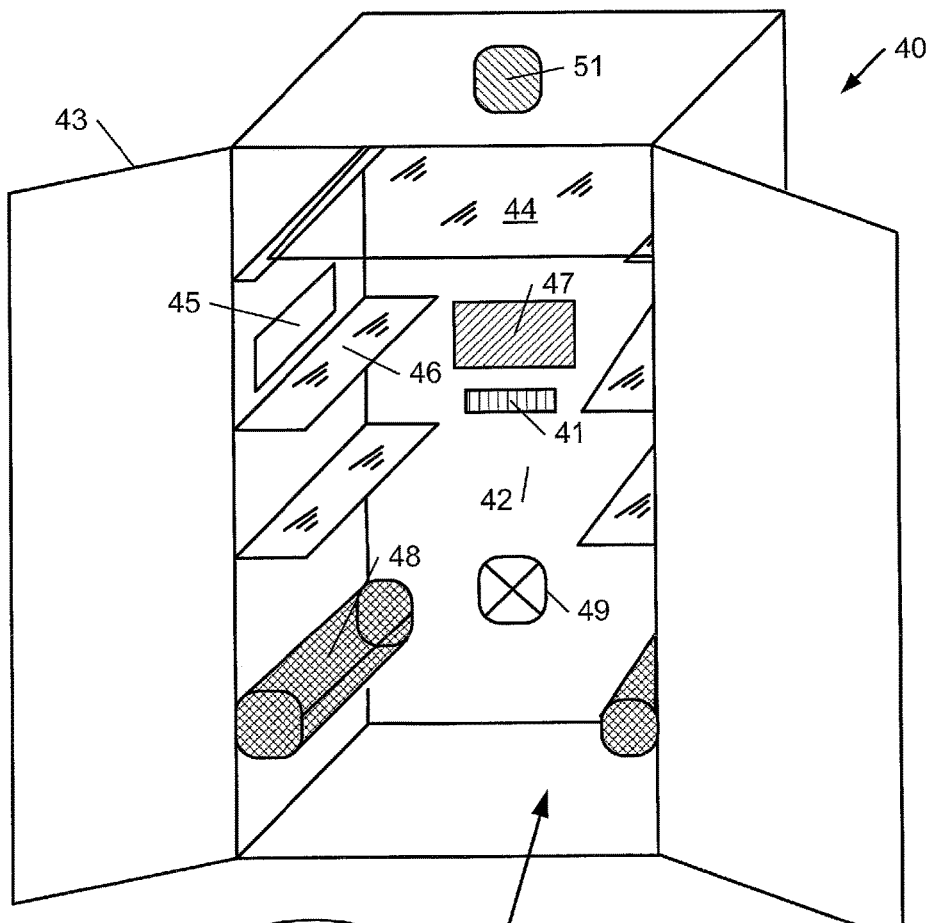
FIG. 3 illustrates a perspective view of an example cabinet for disinfecting one or more objects.
Figure 3:
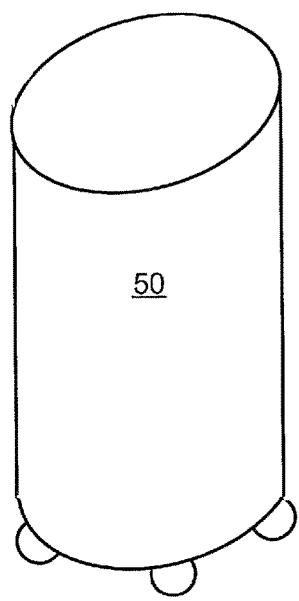

An example of a cabinet having some of the aforementioned features is illustrated in FIG. 3. In particular, FIG. 3 illustrates cabinet 40 having interior void 42 of at least 10 ft$^3$, tray 44, shelving 46 and baskets 48 adjacent the interior void, wherein at least portions of the tray, shelving and baskets facing the interior void are transparent to germicidal light and/or comprise through-holes. In addition, cabinet 40 includes door 43. In some cases, cabinet 40 may include one or more loading ports with closable doors along its exterior sidewalls to access one or more of tray 44, shelving 46 and/or baskets 48 as an additional or alternative manner in which to load one or more objects into the cabinet. An example loading port 45 is shown in FIG. 3 accessing shelving 46. As set forth above, interior void 42 is of sufficient size to accommodate disinfection device 50.

In some embodiments, the cabinets considered herein may have alignment markers and/or an alignment system such that a disinfection device may be placed in a predetermined position within the void of the cabinet as denoted in block 26 of FIG. 1. In some cases, the alignment markers and/or alignment system may be configured such that a germicidal source of the disinfection device is a specified distance from the support structures upon which objects will be placed in the cabinet. In particular, some types of germicidal sources generate intense amounts of heat and, thus, pose a risk of causing items too close to the source of getting too hot to touch after a disinfection process, melting or catching fire. An exemplary range of distances that the alignment markers and/or alignment system may be based on to separate the disinfection device from the support structures may between approximately 3 inches and approximately 12 inches, but shorter and longer distances may be suitable, depending on the germicidal source of the disinfection device.

Various other configurations may be considered for the cabinets as well. For example, in some cases, the cabinets may be absent a floor or, alternatively, include a floor with a tapered lip such that in either case a disinfection device may be easily loaded into the cabinet. In the latter of such embodiments, the cabinet may include a door extending in proximity to the tapered lip. In any case, a cabinet may include a single door by which to load objects and a disinfection device into the cabinet. In other embodiments, cabinet may include multiple doors. For instance, a cabinet may include a first door for primarily loading a disinfection device into the cabinet and a second door for primarily loading objects into the cabinet. In other cases, cabinets that have multiple doors may not have loading designations for their doors. In some embodiments, a cabinet may include doors on opposing sides of the cabinet.

In any case, the cabinets considered herein may, in some embodiments, include a power outlet along its interior for receiving a power plug of a disinfection device. The power outlet may be coupled to a power cord extending out from an exterior surface of the cabinet such that the disinfection device may be coupled to a mains power supply of a building when arranged in the cabinet. Alternatively, a cabinet may include an opening such that a power cord of a disinfection device may be routed therethrough to a power outlet along a wall of a room in which the cabinet is arranged. In yet other cases, a cabinet may be void of such provisions, particularly if the cabinet is specifically designed to accommodate a particular disinfection device that is powered by its own battery.

In some embodiments, the cabinets provided herein may be free-standing units. In other cases, the cabinets may be mounted to a wall. In either case, the cabinets may extend to a floor of a room in which it is arranged, but in other embodiments, they may not. In some embodiments, the sidewalls and doors of the cabinets may be sealed to prevent a germicide generated from a disinfection device therein from leaking out of the cabinet. In other cases, the cabinets may not be sealed. In some embodiments, the cabinets may include a highly reflective material along one or more of its interior surfaces, including the sidewalls, ceiling and/or floor of the cabinet, if applicable. In some cases, the highly reflective materials may be those highly reflective to ultraviolet light and/or visible violet-blue light. In particular, it may be advantageous for at least a portion of the cabinets to include a material which exhibits greater than 50% reflectance to ultraviolet light and/or visible violet-blue light, or more specifically, greater than 85% reflectance to ultraviolet light and/or visible violet-blue light. Examples of reflective materials which may be employed include but are not limited to metalized nylon, Teflon, aluminum, reflective paint, biaxially-oriented polyethylene terephthalate (boPET) (e.g., Mylar), and GORE® DRP® Diffuse Reflector Material available from W. L. Gore & Associates, Inc. In addition or alternative to being highly reflective, the cabinets may include a variety of other material characteristics along its interior surface, such as but not limited to being antimicrobial.

In some cases, the cabinets described herein may include one or more fans, such as shown by reference number 49 in FIG. 3, for cooling the interior of the cabinets and/or dispersing a liquid or gas germicide generated by a disinfection device arranged in the cabinet FIG. 3. The one or more fans may be arranged interior to the cabinet and/or may be arranged within the sidewalls, floor or ceiling of the cabinet. In embodiments in which the cabinet includes one or more fans arranged within its walls, the fans may be configured to drawn air in or out of the cabinet. In some cases, the cabinet may include an ozone reducing device disposed within a wall, floor or ceiling of the cabinet extending between an interior of the cabinet to an exterior of the cabinet such as shown by reference number 51 in FIG. 3. In particular, ozone may, in some cases, be created as a byproduct from the use of a germicidal light source, specifically if the lamp generates ultraviolet light of wavelengths shorter than approximately 240 nm since such a spectrum of UV light causes oxygen atoms of oxygen molecules to dissociate, starting the ozone generation process. Ozone is a known health and air quality hazard and, thus, the release of it by devices is regulated. Examples of ozone reducing devices which may be included in the cabinets described herein include but are not limited to a carbon filter or a device which produces free radicals catalysts that covert ozone to diatomic oxygen.

In some embodiments, the cabinets described herein may include one or more germicide dose sensor/s, such as shown by reference number 41 in FIG. 3 for detecting the amount of germicide dispersed in the cabinet. In some cases, the germicide dose sensor/s may be configured to affect the operation of a disinfection device arranged in the cabinet. In particular, the cabinet and/or the disinfection device may include a storage medium with processor executable program instructions to shut off the disinfection device when a signal is received from the germicide dose sensor/s indicating that a predetermined dose of germicide is detected within the cabinet as denoted in block 30 of FIG. 1. In additional or alternative embodiments, the cabinets described herein may include a humidity and/or temperature control system, such as shown by reference number 47 in FIG. 3. In particular, the cabinets described herein may include dehumidifiers and/or cooling devices to control the humidity and temperature of the interior of the cabinet. In particular, controlling the humidity and/or temperature of an environment sometimes may improve the germicidal efficacy of a germicidal source and, thus, may be used to optimize disinfection cycle time.

In some cases, the cabinet may include a system for identifying objects placed in the cabinet to ensure objects placed in the cabinet are those that have been deemed suitable for a particular disinfection system. In some embodiments, a system for identifying objects may include a scanning system, such as a barcode reader or an RF receiver, that is used to identify objects placed in the cabinet having identification tags attached thereto. In addition or alternatively, a system for identifying objects may include a weight sensor in one or more of the support structures of the cabinet. In particular, a weight sensor may be used to verify whether the weight of an object placed on or in the support structure is in an appropriate range for what it has been identified as via a scanning system of the cabinet. In addition or alternatively, a support structure of the cabinet may be designated for receipt of a particular object (or a particular type of object, such as a type of medical device) and the weight sensor may be used to verify whether the weight of an object placed in or on the support structure is in an appropriate range for the object which support structure is designated. In some of such cases, the support structure may have sidewalls having a peripheral contour similar to the object for which it is designated as described in more detail below in reference to FIGS. 9 and 10. In other embodiments, the support structure may not have a distinct shape, but yet be designated for a particular object or object type for verification purposes. In any case, the cabinets described herein may include a system to ensure objects on the support structures of the cabinet are not touching each other, such as but not limited to a machine vision system.

In some embodiments, the cabinets provided herein may include a user interface. The user interface may be used for setting disinfection process parameters and/or communicating conditions of various systems comprising the cabinet, including but not limited to process parameters and/or conditions for any of the features noted above. In general, the user interface may be configured to project audio commands (i.e., have a speaker and program instructions for sending signals for an audio command to be broadcasted) and/or display visual commands (i.e., include as screen and program instructions for displaying text or pictorial information thereon) for setting disinfection process parameters and/or communicating conditions of various systems comprising the cabinet. It is noted that the aforementioned features of chamber 40 described in reference to FIG. 3, namely the shelving, basket/s, tray/s, user interface, identification system, weight sensor, germicide dose sensors, humidity and/or temperature controllers, ozone filter, fans and loading ports, are optional and are not mutually inclusive.

Figure 4:
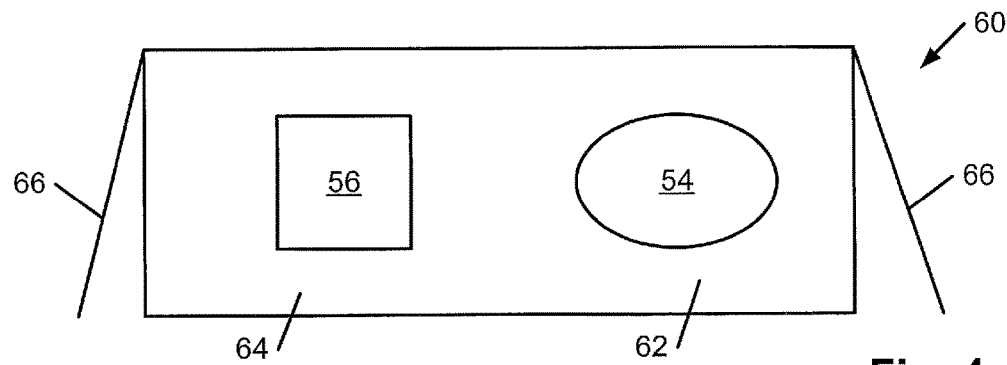
FIG. 4 illustrates a schematic top view of another example cabinet for disinfecting one or more objects.

As shown in FIG. 3 and described above, the configuration of cabinet 40 is specific to having void 42 substantially central to cabinet 40 with tray 44, shelves 46 and baskets 48 arranged around void 42. The cabinets described herein, however, are not necessarily so limited. In particular, cabinets considered herein may have off-center void regions for accommodating a disinfection device. FIG. 4 illustrates a top view schematic drawing of cabinet 60 having disinfection device 54 disposed off-center in the cabinet, particularly in portion 62 of the cabinet opposing portion 64 having one or more objects 56 disposed therein. In general, one or more objects 56 may include object/s of any configuration (i.e., shape, size, weight, material, construction, etc.). In some cases, object/s 56 may be disposed on tray/s, shelving and/or basket/s arranged in portion 64. In some of such cases, the tray/s, shelving and/or basket/s may be arranged along interior surfaces of portion 64 such as described for the tray/s, shelving and/or baskets of cabinet 40 in FIG. 3. In addition or alternatively, the tray/s, shelving and/or basket/s may be supported by a free-standing rack arranged in portion 64 of cabinet 60. In some cases, the free-standing rack may include wheels or some other displacement mechanism to affect mobility and portability of the rack. In such embodiments, the rack may be preloaded with one or more objects 56 prior to being placed in portion 64 of cabinet 60. In other cases, the rack may not include a displacement mechanism and, in some embodiments, the rack may be secured within cabinet 60.

In alternative embodiments, one or more objects 56 may be placed on the floor of cabinet 60 or the floor upon which the cabinet is arranged. In such cases, one or more objects 56 may not be placed on a specific support structure within cabinet 60. In some of such embodiments, one or more of object/s 56 may include wheels or some other displacement mechanism to affect mobility and portability of the object/s. Alternatively, one or more of object/s 56 may be void of displacement mechanisms. In any case, to accommodate a rack or free standing objects within portion 64, portion 64 may include a void space sufficient to receive the rack or free-standing object. The void space may be on the order of greater than approximately 1.0 ft$^3$, greater than approximately 5.0 ft$^3$ and, in some cases, greater than approximately 10.0 ft$^3$, but smaller void spaces may be considered.

As noted above in reference to FIG. 3, some of the cabinets disclosed herein may include a void space greater than approximately 10.0 ft$^3$ to accommodate a disinfection device generally configured for room disinfection. In some embodiments, portion 62 may include such a void space. In other cases, however, disinfection device 54 need not be so large and, thus, portion 62 may be smaller than 10.0 ft$^3$. In general, disinfection device 54 may include any device configured to generate a dispersible germicide. Although disinfection device 54 may be configured to be independently operational from cabinet 60 and/or may be configured for room disinfection, disinfection device 54 need not be so limited. In particular, disinfection device 54 may, in some embodiments, be operationally dependent on cabinet 60, specifically that the power used to operate the device is drawn through the cabinet. In addition or alternatively, disinfection device 54 need not include all or any of the features described above that are generally associated with room disinfection devices.

As shown in FIG. 4, cabinet 60 may include doors 66 for allowing separate access to portions 62 and 64. Such a configuration may ease loading of one or more objects 56 and disinfection device 54 into the cabinet. In alternative embodiments, however, cabinet 60 may include a single door. In addition or alternatively, cabinet 60 may include closable loading ports along its exterior surface aligned with support structures in portion 64 when cabinet 60 includes such support structures. In any case, the door/s and/or loading port/s may be arranged along any portion of the cabinet and, thus, the positions of the door/s and loading port/s should not be limited to be on opposing ends of the cabinet as shown in FIG. 4. Furthermore, the door/s and loading port/s of the cabinet may be hinged doors, sliding doors, or retractable doors and, thus, should not be limited to the hinged doors shown in FIG. 4.

Figure 5:
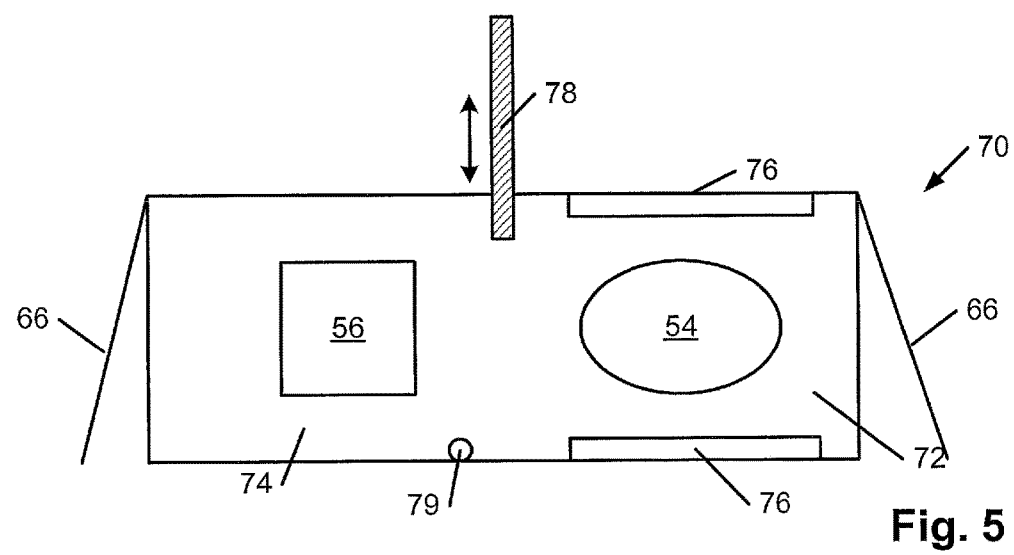
FIG. 5 illustrates a schematic top views of an example cabinets having partitionable chambers for disinfecting one or more objects.

Although portion 62 of cabinet 60 is shown absent of object/s therein, use of the cabinet should not be so limited. In particular, one or more objects may be placed in portion 62 as long as they do not interfere with the arrangement of disinfection device 54. FIG. 5 illustrates cabinet 70 having support structures 76 (i.e., tray/s, shelving and/or baskets) arranged adjacent to disinfection device 54 in portion 72 of the cabinet. In addition, cabinet 70 includes portion 74 having one or more objects 56 placed therein as similarly described for one or more objects 56 in portion 64 of cabinet 60 in FIG. 4. To increase efficiency, it may be advantageous in some cases to successively load one or more objects into portions 72 and 74 of cabinet 70. In such embodiments, it may be advantageous to partition portion 74 from portion 72 such that the one or more objects placed in portion 72 may be disinfected from a germicide projected from disinfection device 54 while one or more objects 56 are placed into portion 74. As such, cabinet 70 includes moveable partition 78 to separate portions 72 and 74 of cabinet 70.

In general, moveable partition 78 is configured to block transmission of a germicide generated by disinfection device 54. In embodiments in which the germicide is a liquid, gas, mist or plasma, any non-pervious material may be used for partition 78, such as glass, plastics, metals, or wood. In some of such cases, at least the side of partition 78 facing disinfection device 54 may include a material which is resistant to chemical erosion. In other cases, particularly in which the germicide generated by disinfection device 54 is germicidal light, at least the side of partition 78 facing disinfection device 54 may include a material which attenuates the germicidal light. Further to having partition 78, cabinet 70 may, in some embodiments, include sensor 79 for detecting when partition 78 is in position to separate portions 72 and 74 of the cabinet.

Figure 6:
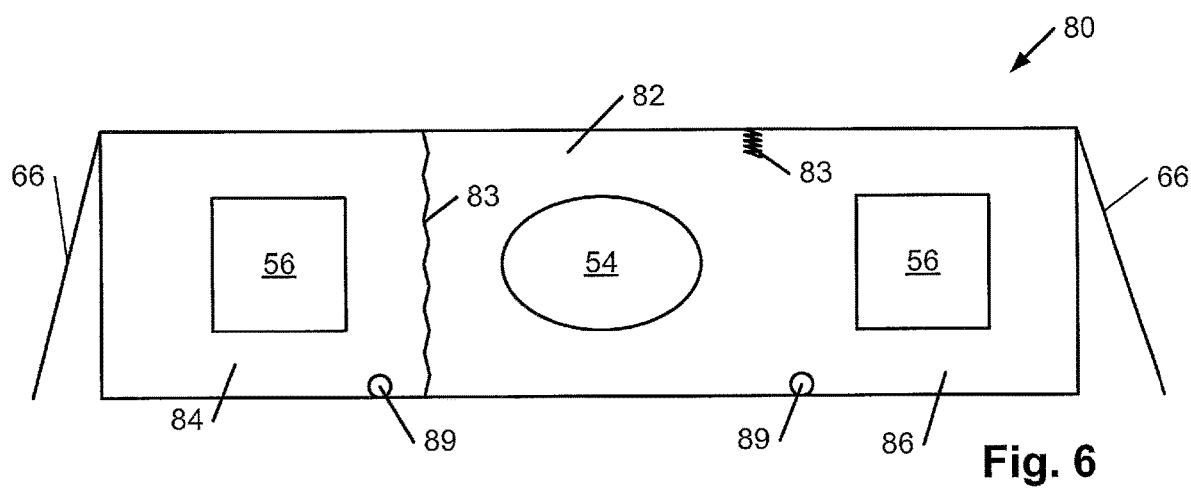
FIG. 6 illustrates a schematic top view of another example cabinet having partitionable chambers for disinfecting one or more objects.
Figure 7:
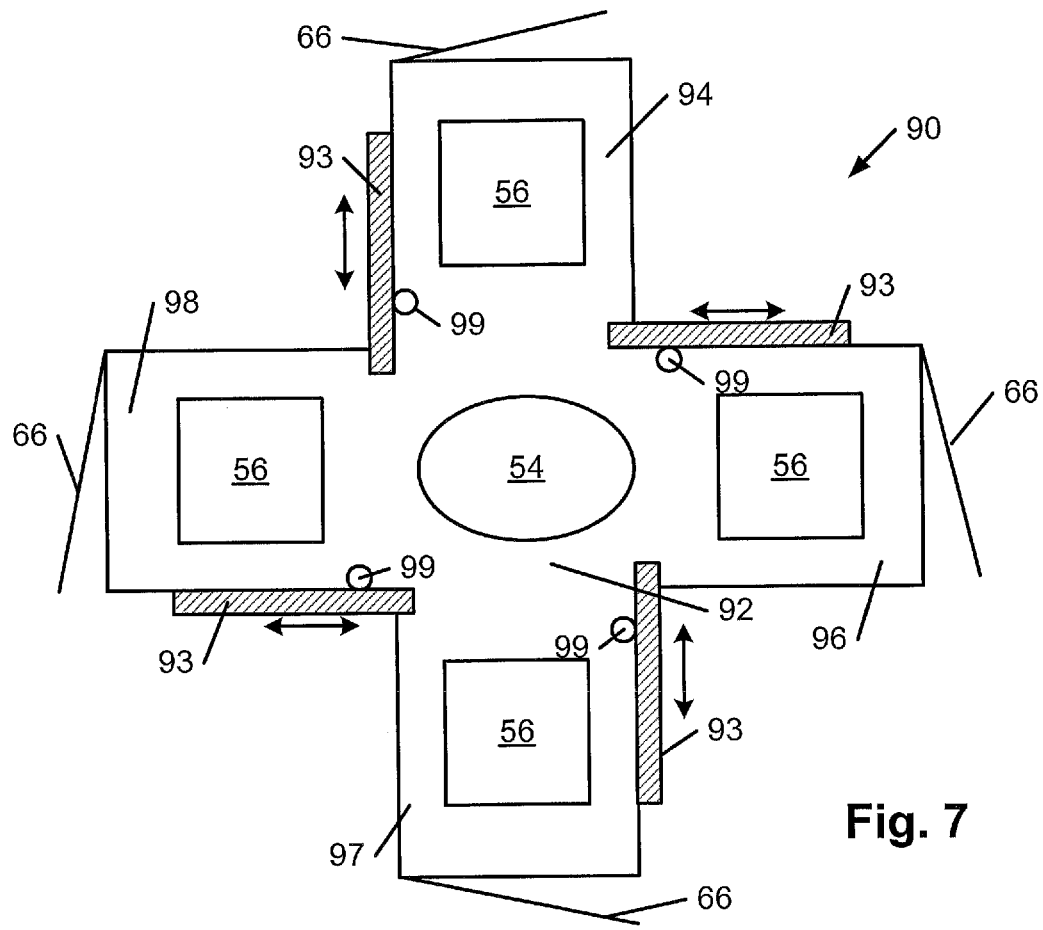
FIG. 7 illustrates a schematic top view of another example cabinet having partitionable chambers for disinfecting one or more objects.

Cabinets with more than one partition are illustrated in FIGS. 6 and 7. In particular, FIG. 6 illustrates cabinet 80 having moveable partitions 83 respectively separating portions 84 and 86 from portion 82 and sensors 89 for detecting when partitions 83 are in position to respectively separate portions 84 and 86 from portion 82. In addition, FIG. 7 illustrates cabinet 90 having moveable partitions 93 respectively separating portions 94, 96, 97, and 98 from portion 92. Furthermore, FIG. 7 illustrates cabinet 90 having sensors 99 for detecting when partitions 93 are in position to respectively separate portions 94, 96, 97, and 98 from portion 92. As respectively shown in FIGS. 6 and 7, portions 82 and 92 accommodate disinfection device 54 and each of portions 84, 86, 94, 96, 97 and 98 accommodate one or more objects 56. Moreover, each of cabinets 80 and 90 include doors 66 for respectively accessing portions 84, 86, 94, 96, 97 and 98. In some cases, cabinet 80 and/or cabinet 90 may include an additional door for loading disinfection device 54. It is noted that partitions 83 differ from partition 78 of cabinet 70 and partitions 93 of cabinet 90 in that they are retractable within the cabinet. The variation of the partitions, however, is not specific to the configuration of cabinet 80 nor are partitions 78 and 93 specific to cabinets 70 and 90. Any type of moveable partition may be employed in the cabinets described herein, including but not limited to those shown in FIGS. 5-7 but as well as those which move vertically from or through the ceiling of the cabinets or from the floor of the cabinet. Moreover, portions 84, 86, 94, 96, 97 and 98 need not be the same size within a cabinet.

Figure 8:
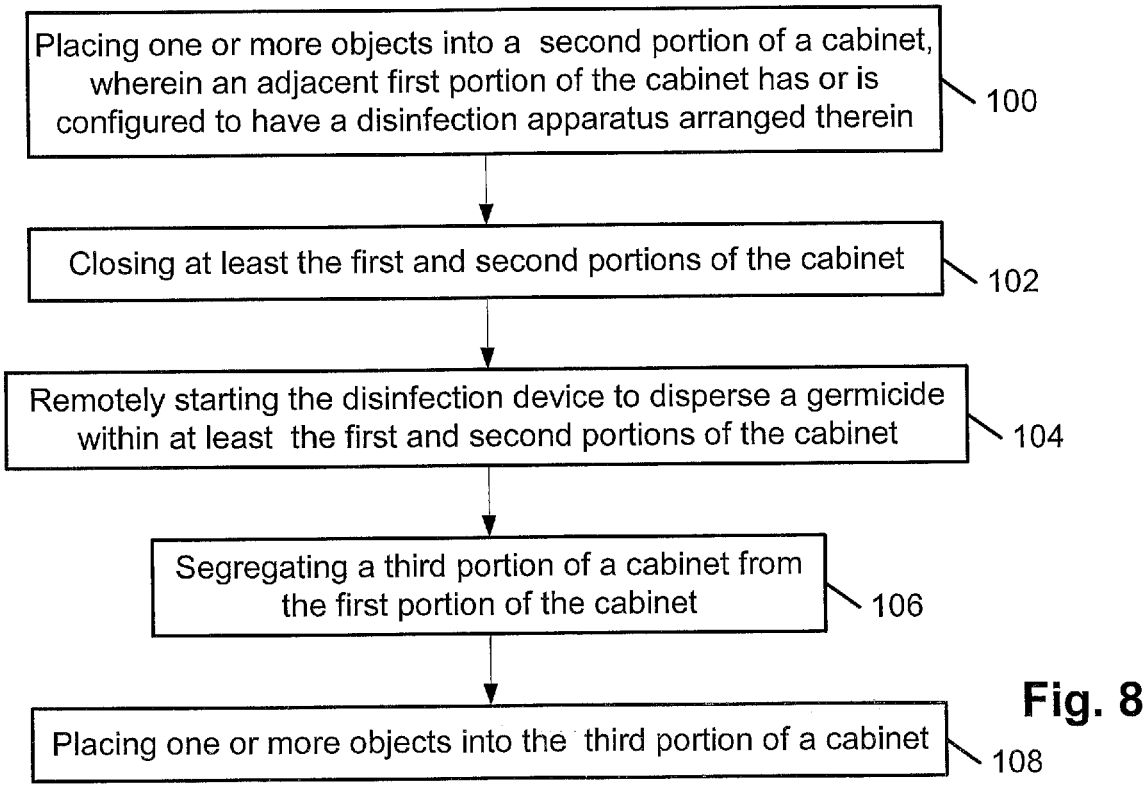
FIG. 8 illustrates an example flowchart of a method for disinfecting one or more objects in a cabinet having partitionable chambers.

A method of disinfecting objects within cabinets having partitionable portions or chambers, such as shown and described above in reference to FIGS. 6 and 7, is shown in FIG. 8. In particular, FIG. 8 includes block 100 in which one or more objects are placed into a second portion of a cabinet, which is adjacent a first portion of a cabinet having a disinfection device arranged therein or at least configured to accommodate a disinfection device. In the latter of such embodiments, a disinfection device may be placed within the first portion of the cabinet during or after the one or more objects are placed into the second portion of the cabinet. In any case, the method continues with closing at least the first and second portions of the cabinet as denoted in block 102. Subsequently in block 104, the disinfection device is remotely started to disperse a germicide within at least the first and second portions of the cabinet.

At some point before, during or after any of the processes denoted in blocks 100, 102 and 104, a third portion of the cabinet is segregated from the first portion of the cabinet (i.e., the portion of the cabinet designated to house the disinfection device) using a germicide blocking partition, such as those described above in reference to FIGS. 5-7. After such segregation, one or more objects are placed into the third portion of the cabinet as denoted in block 108 of FIG. 8. Due to the germicide blocking partition, the process of block 108 may, in some cases, be performed while the disinfection device is generating and projecting a germicide into the first and second portions of the cabinet. Such a method may be similarly facilitated for other chambers of the cabinet such that there may be a succession of simultaneous loading the cabinet with object/s and disinfecting object/s within the cabinet among the different chambers. In addition, portions of a cabinet may also be segregated after disinfecting objects therein such that the objects may be removed from the cabinet while objects in a different portion of the cabinet are being disinfected.

Further to the idea of ensuring objects placed in a cabinet are those that have been deemed suitable for a particular disinfection system, support structures are provided which are configured to confirm an object placed thereon/therein is suitable for a particular disinfection system. In particular, support structures are provided which include sidewalls shaped to emulate a peripheral contour of a particular object, such as a medical device. The sidewalls may be sidewalls of a base of a support structure or may extend up from the base of the support structure. In some embodiments, the periphery of the support structure and the areal space of the base may be slightly larger than the object it is configured to receive. In this manner, the object may be inset within the support structure in cases in which the sidewalls of the support structure extend up from the base. In other embodiments, the periphery of the support structure and the areal space of the base may be substantially equal or smaller than the object it is configured to receive. In such cases, the object may be suspended above the base of the support structure when the sidewalls of the support structure extend up from the base.

Figure 9:
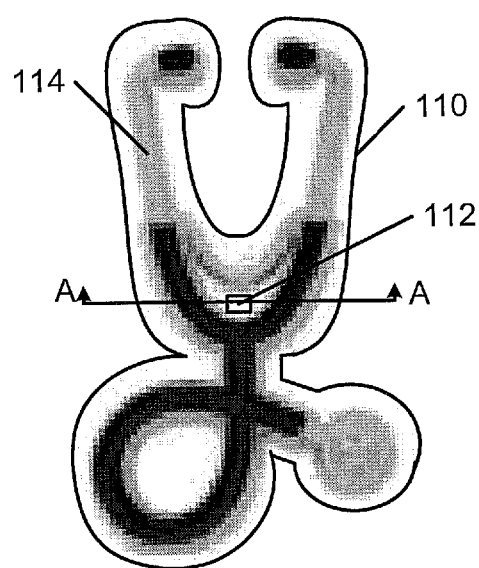
FIG. 9 illustrates an example a top view of an example basket designed to hold a stethoscope.
Figure 10:
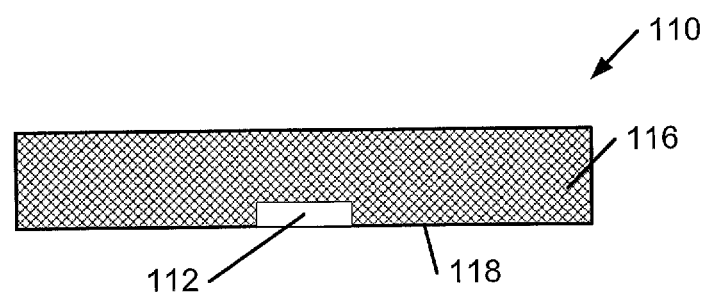
FIG. 10 illustrates a cross-sectional view of the example basket shown in FIG. 9 taken along axis A-A.

In any case, the configuration of the sidewalls to match a peripheral contour of a particular object offers visual confirmation that the object has been deemed suitable for the particular disinfection system the support structure comprises. In some cases, the support structure may additionally include contour sensors along its base and/or sidewalls to electronically confirm the peripheral contour of an object placed on the support structure matches that of the specifically shaped sidewalls. In any case, the support structure may include a shelf, basket or a tray. An example of a support structure having such features is illustrated in FIGS. 9 and 10. In particular, FIGS. 9 and 10 illustrate basket 110 having base 118 with sidewalls 116 extending up from the base and shaped to match a peripheral contour of stethoscope 114. In some cases, the base and/or sidewalls may include materials transparent to germicidal light and/or one or more through-holes for the transmission of germicide therethrough.

In some cases, the support structure may include a weight sensor, such as shown with weight sensor 112 in FIGS. 9 and 10, to verify whether the weight of an object placed on the support structure is in an appropriate range for what it has been designed to receive. In addition or alternatively, the support structure may include a scannable identification tag to coincide with a scanning identification system of a cabinet in which the support structure is to be arranged. In any of such cases, the support structure may, in some cases, include a means for conveying information to a user of the support structure (e.g., via visual display and/or audio commands) of the state of such various features. In some of such embodiments, the support structure may include a processor and a storage medium comprising program instructions executable by the processor for activating said means for conveying information upon receiving signal/s from the various features. For example, the support structure may include processor executable program instructions for activating said means for conveying information upon the weight sensor detecting a force that exceeds a predetermined threshold and/or upon a multiple of the contour sensors detecting contact with an object.

As noted above, other examples of systems, cabinets and methods for disinfecting objects are provided in FIGS. 11-14, particularly ones which are configured to enable a germicidal source to be inserted into a cabinet while retaining at least a portion of a base supporting the germicidal source exterior to the cabinet. In particular, FIG. 11 illustrates cabinet 120 having exterior structure 122, port 124, door 126 and air vents 128. As shown in FIG. 11, exterior structure 122 is configured such that voided space 130 is arranged below port 124. Voided space 130 is dimensionally configured to receive and accommodate at least a portion of a base of a disinfection apparatus and, in some cases, all of the base or the entire disinfection apparatus. As further shown in FIG. 11, port 124 may, in some embodiments, extend out of cabinet 12, past the exterior surface of exterior structure 122. In other cases, however, port 124 may be inset or flush with the exterior structure 122.

As set forth in more detail below in reference to FIGS. 12 and 13, a germicidal source of a disinfection apparatus is inserted into port 124 when the disinfection apparatus is placed in voided space 130. In order to accommodate the insertion of the germicidal source, either port 124 and/or portions 123 of exterior structure 122 above voided space 130 may be configured to move. For example, portions 123 of exterior structure 122 may include a pliable material, such as a fabric or any non-textile pliable material. In this manner, the portion of exterior structure 122 above voided space 130 and port 124 attached thereto may be moved up when a disinfection apparatus is placed into voided space 130 and then moved down around the germicidal source thereafter. In some embodiments, additional portions of exterior structure 122 or all of exterior structure 122 may be made of one or more pliable materials. In such cases, cabinet 122 may include a frame to support the pliable material/s. The frame may be exterior or interior to the pliable material.

In additional or alternative embodiments, portions 123 of exterior structure 122 above voided space 130 as well as port 124 may be configured to open, particularly along but not limited to a face of the exterior structure 122 and/or port 124 that is in the direction in which a disinfection apparatus is to be received. For example, a front, side and/or back facing portion of exterior structure 122 above voided space 130 and/or a front, side and/or back facing part of port 124 may include a zipper or another type of fastener system (such as but not limited to Velcro, snaps, and magnets) to open and close adjoining flaps of either exterior structure 122 and/or port 124. In other cases, the front, side or back facing parts of port 124 and/or the portions of exterior structure 122 above voided space 130 may include doors, particularly if they are made of rigid materials. In any case, closable openings afforded along front, side or back facing parts of port 124 and/or portions 123 of exterior structure 122 may allow a germicidal source of a disinfection apparatus being received into voided space 130 to be inserted into cabinet 122 and then surrounded by port 124 and portions 123 of exterior structure 122.

In general, the size of voided space 130 may vary depending on the design specifications of cabinet 120. In some cases, the size of voided space 130 may be particularly designed for dimensional characteristics of a particular disinfection apparatus to be used with cabinet 120. In other embodiments, the size of voided space 130 may not be specific to a particular disinfection apparatus. In either case, provisions, such as a shelf, may be added to voided space 130 to accommodate disinfection apparatuses that are not tall enough to have their germicidal source inserted into the cabinet via port 124. More specifically, a shelf may be placed on the floor of voided space 130 or affixed to a wall of exterior structure 122 in voided space 130 such that relatively small disinfection apparatus may be used in accompaniment with the cabinet to disinfect object/s therein.

Although exterior structure 122 is shown having support beams on the outer corners of voided space 130, the support beams may be omitted from cabinet 120 if they are not needed for structural support. In this manner, there may be fewer restrictions on the width of the disinfection apparatuses that may be received into voided space 130. Although the cabinets described herein should not be so limited, in some embodiments, cabinet 120 may be used in accompaniment with a disinfection apparatus configured for room/area disinfection for the disinfection of objects therein. In such cases, a general and example range of width, depth and height dimensions for voided space 130 may be between approximately 2 feet and approximately 4 feet each, but smaller or larger dimensions may be considered.

As shown in FIG. 11, exterior structure 122 may be configured such that the floor of voided space 130 is substantially level with the floor of the room in which the cabinet is arranged. In particular, exterior structure 122 may be configured such that the floor of voided space 130 is the floor of the room or includes a flooring of cabinet 120 substantially level with the floor of the room. In either case, such a configuration may facilitate ease for receiving a disinfection apparatus into voided space 130 having wheels to affect its mobility, as is commonly associated with but not necessarily limited to room/area disinfection apparatuses. In yet other cases, the floor of voided space 130 may be arranged above the floor of a room in which the cabinet is arranged. For example, in some embodiments, the floor of voided space 130 may be a fraction of an inch or even more than an inch above the floor of the room in which the cabinet is arranged. In such cases, the floor of voided space 130 may, in some embodiments, include a tapered lip such that a disinfection device with wheels may be easily loaded into space. In yet other cases, the floor or voided space 130 may be arranged more than a few inches above the floor of the room in which the cabinet is arranged. In such embodiments, the floor of voided space 130 may, in some cases, include a ramp such that a disinfection device with wheels may be more easily loaded into space. In yet other embodiments, the floor of voided space 130 may not include a ramp or a tapered lip.

In any case, the cabinets described herein are not restricted to being used with disinfection apparatus having wheels and, thus, in some embodiments, the floor of voided space 130 may be arranged a foot or more above a floor of the room in which the cabinet is arranged. In some cases, a cabinet may have a voided space with a floor arranged between approximately 2.5 and approximately 3.5 feet above a floor of the room in which the cabinet is arranged. Such a configuration may be ergonomically advantageous in embodiments in which a disinfection apparatus that is easily carried by a human is used in accompaniment with the cabinet to disinfection objects therein. In particular, having a voided space with a floor within such a height range may inhibit the human from having to bend to position the apparatus in the voided space.

As noted above, exterior structure 122 is configured such that voided space 130 is arranged below port 124, particularly in embodiments in which port 124 is arranged along a surface of exterior structure 122 that is parallel with a floor in which cabinet 120 is arranged. The cabinets disclosed herein, however, are not limited to such a location of port 124. On the contrary, port 124 may be alternatively arranged along a surface of exterior structure 122 that is perpendicular with a floor in which cabinet 120 is arranged. An example of such a cabinet is shown in FIG. 14 and described in more detail below. In yet other embodiments, port 124 may be arranged along a surface of exterior structure 122 that is at an angle between 0° and 90° with a floor in which cabinet 120 is arranged. In either of such cases, depending of the configuration of the disinfection apparatus and, more particularly, depending how far a disinfection apparatus is configured to extend a germicidal source beyond the confines of its base, cabinet 120 may not have a voided space to accommodate a base of a disinfection apparatus (such as voided space 130).

Regardless of the position of port 124 along exterior structure 122 of cabinet 120, port 124 may have a periphery that surrounds a portion of an item partially inserted into the port. In general, port 124 may be annular, meaning it is or forms an encircling structure around an opening. Although the inner and/or outer edges of port 124 may be circular, the term "annular", as used herein, is not limited to having circular outer or inner edges. On the contrary, port 124 may have inner and outer edges of any shape. In some cases, the periphery of port 124 may be dimensionally adjustable as is denoted by the arrowed lines on port 124 in FIG. 11. In this manner, the periphery of port 124 may be widened to allow an item of a particular size to be easily inserted through the port. Examples of materials or items which may be employed at the periphery of port 124 to impart adjustable dimensions include but are not limited to elastic rings, adjustable width clamps, and Velcro straps. In some additional or alternative embodiments, the periphery of port 124 may be configured to come into contact with a portion of an inserted item that has a width within a particular range. For example, port 124 may include an adjustable periphery that can adjust down to a width within a particular range. In addition or alternatively, the periphery of port 124 may include fasteners, such as but not limited to snaps, magnets, and hooks or loops, for attaching to a portion of an item partially inserted therein. In some cases, the disinfection apparatus partially inserted into port 124 may have matching fasteners around a designated portion thereof to mate with fasteners along the periphery of port 124.

In some embodiments, the periphery of port 124 may be configured to conform to a periphery of an item partially inserted therein such that the periphery substantially seals the port against the item. The term "substantially seal", as used herein, refers to joining multiple items to a sufficient degree such that there is negligible transmission of fluids therethrough. For example, in an embodiment in which port 124 is substantially sealed against a portion of a disinfection apparatus with its germicidal source inserted into cabinet 120, the term "substantially sealed" in such a context means that that less than 1% of germicide generated by a germicidal source in the cabinet is transmitted through the joined interface of the port and the disinfection apparatus. Regardless of the manner the periphery of port 124 is configured to encircle an item, the dimensions and materials used to constitute port 124 may vary depending on the design specifications of cabinet 120 and, more specifically, the dimensions of the disinfection apparatus/es to be employed with cabinet 120. An example range of widths which port 124 may be configured to accommodate is between approximately 6 inches and approximately 18 inches, but smaller and larger dimensions as well as wider and narrower ranges may be considered.

In addition to port 124, cabinet 120 includes another port for loading items into interior space 132 of cabinet. As shown in FIG. 11, the loading port include door 126. Although door 126 is shown as a retractable rolling door, the door is not necessarily so limited. In particular, door 126 may alternatively be a sliding door, an accordion door, a hinged door or a flap door (which may be fastened to the side edge of cabinet 120 when loading items into interior space 132). In cases in which cabinet 120 is to be used in a small or narrow space, such as a hallway for example, it may be advantageous for cabinet 120 to include a retractable door, an accordion door or a flap door to access interior space 132 to minimize the area occupied by the door when opened. In any case, cabinet 120 may include a single door for accessing interior space 132 as shown in FIG. 11 or, alternatively, may include multiple doors. In either embodiment, the door/s may be arranged along any side (i.e., the front, side or back) of cabinet 120.

As shown in FIG. 11, the floor of interior space 132 may be substantially level with the floor of the room in which the cabinet is arranged and door 126 may extend to a floor of cabinet 120. In embodiments in which cabinet 120 does not include a floor, door 126 may extend to a floor of a room in which the cabinet is arranged. In either case, door 126 may, in some embodiments extend up to a height of 5 feet or more. Such configurations may ease the loading of items into interior space 132. In particular, having door 126 extend to a floor of cabinet 120 or the floor of the room may ease the loading of items having wheels or items carried into interior space 132 by a human. In addition, having door 126 extend to a height of 5 feet or more may generally allow a person to at least partially enter interior space 132 to place items therein. In yet other cases, cabinet 120 may have a floor arranged above the floor of a room in which the cabinet is arranged. In such cases, the floor of cabinet 120 may, in some embodiments, include a tapered lip or a ramp such that an item with wheels may be easily loaded into interior space 132.

In any case, configurations to have door 126 extend to a height of 5 feet or more and extend down to or close to the floor of the cabinet or room in which the cabinet is arranged allows relatively large items (i.e., items occupying more than approximately 1.0 ft$^3$ or even those occupying more than 5.0 ft$^3$) to be loaded into interior cavity 132 (i.e., as long as the width of door 216 and the depth of cabinet 120 are appropriately sized to accommodate such items). Example dimension ranges of the width of door 216 and the depth of cabinet 120 to be able to accommodate relatively large items may be between approximately 2 feet and approximately 5 feet each. Accordingly, the area of interior space 132 may sometimes be greater than 20 ft$^3$ or even greater than 30 ft$^3$. In cases in which cabinet 120 is to be used in a small or narrow space, such as a hallway for example, it may be advantageous to limit the depth of cabinet 120 to be between approximately 2 feet and approximately 5 feet and the overall length of cabinet 120 to be between approximately 6 feet and approximately 8 feet. In any case, examples of relatively large items which are commonly used in hospitals and which may be well suited to be disinfected in cabinet 120 include but are not limited to wheelchairs, mobile work stations, vital sign monitors, wheeled over-the-bed tables, intravenous poles, carts, isolettes, ultrasounds, and ventilators.

Although cabinet 120 is shown in FIG. 11 and described above particularly for the disinfection of relatively large items, the features of cabinet 120 described above (i.e., port 124 and voided space 130) to enable a germicidal source to be inserted into a cabinet while retaining at least a portion of a base supporting the germicidal source exterior to the cabinet may be employed in a cabinet specifically configured to disinfect relatively small objects (i.e., objects occupying less than approximately 1.0 ft$^3$ and, in some cases, objects occupying less than approximately 0.5 ft$^3$). As such, in some of such embodiments, the interior space of the cabinet may be substantially smaller than that described for cabinet 120 of FIG. 11. Furthermore, door 126 need not extend to a floor of a room in which the cabinet is arranged or extend up to a height of 5 feet or more. In some embodiments, cabinet 120 may be used to disinfect multiple items at the same time, including any combination of multiple large items and/or multiple small items as long as space permits in interior space 132.

In any case, cabinet 120 may include air vents 128 to exhaust heat out of the cabinet. As shown in FIG. 11, air vents 128 may, in some embodiments, be arranged along an upper portion of cabinet 120, particularly along the ceiling and/or the upper sidewalls of the cabinet, since hot air rises. In some cases, however, cabinet 120 may additionally or alternatively include air vents on lower sidewalls of the cabinet and/or along a floor of the cabinet if the floor of the cabinet is elevated above the floor in which the cabinet is arranged. Furthermore, cabinet 120 may include any number of air vents, including a single air vent or any plurality of air vents. In addition, cabinet 120 need not include air vents grouped in clusters of three as shown in FIG. 11. Thus, the location, number and relative arrangement of air vents in cabinet 120 should not be limited to the depiction of air vents 128 in FIG. 11. In any case, air vents may generally include filters to prevent germicide generated in cabinet 120 from exiting air vents into the external ambient of the cabinet.

As noted above, the cabinets described herein may include a variety of features, including a highly reflective material along one or more of its interior surfaces, including the sidewalls, ceiling and/or floor of the cabinet, if applicable. As such, cabinet 120 may include a highly reflective material along one or more of its interior surfaces, including the sidewalls, ceiling and/or floor of the cabinet. In some cases, the highly reflective materials may be those highly reflective to ultraviolet light and/or visible violet-blue light. In addition or alternative to being highly reflective, cabinet 120 may include a variety of other features generally described above for cabinets described herein. For example cabinet 120 may include any number and combination of shelving, basket and/or trays attached to its sidewalls and/or ceiling. Other features that are described above and which cabinet 120 may include are door sensors, motion or occupancy sensors, alignment markers, power outlet, power cord, user interface, fans, ozone filters, germicidal dose sensor (such as shown by reference numeral 134 in FIG. 11), humidity and/or temperature control systems, object identification systems, and moveable partitions. The descriptions of such features are referenced from above for cabinet 120 and are not reiterated for the sake of brevity. Furthermore, cabinet 120 may be a free-standing unit or may be a wall mounted unit. Moreover, cabinet 120 may, in some embodiments, be a construct which is not readily mobile. In other embodiments, cabinet 120 may be configured for mobility, such as but not limited to being readily collapsible and/or having wheels along its bottom portion.

As set forth above, voided space 130 and interior space 132 are sized to accommodate a portion of disinfection apparatus and an item to be disinfected, respectively. An example of a disinfection apparatus and an item to be disinfected that may be used in accompaniment with cabinet 120 are shown in FIG. 11 with double arrowed lines indicating the apparatus and item may be positioned in and out of voided space 130 and interior space 132, respectively. As shown in FIG. 11, wheelchair 138 may be an item disinfected in cabinet 120. Other items, including larger or smaller items, however, may be considered. FIG. 11 further illustrates disinfection apparatus 140 having germicidal source 142 extending out from base 144. Germicidal source 142 may include any of the germicidal sources described above for the disinfection apparatuses disclosed herein. The descriptions of such germicidal sources are referenced from above for germicidal source 142 and are not reiterated for the sake of brevity.

It is noted that germicidal source 142 and base 144 may be of any shape or size and, thus, germicidal source 142 and base 144 should not be limited to the depiction of disinfection apparatus in FIG. 11. Furthermore, in some cases, germicidal source 142 may include a casing around the source of the germicide it is configured to emit and, thus, in some embodiments, both a source of a germicide and casing surrounding the source of the germicide may be inserted into port 124 of cabinet 120. For example, in embodiments in which germicidal source 142 includes a source of germicidal light, germicidal source may, in some cases, include a transparent barrier around the source of light. The transparent barrier may serve to protect the source of light from damage and/or provide a plenum through which a cooling fluid may be transported.

In addition to supporting germicidal source 142, base 144 of disinfection apparatus 140 includes components 148 operationally coupled to the germicidal source for operation thereof and also air moving device 146 for drawing air into base 144 from the ambient of the base. Components 148 may include any mechanisms and program instructions to facilitate the generation and dispersal of germicide from germicidal source 142. The number and types of components included in base 144 will generally depend on the germicide the germicidal source is configured to generate and further on the design specifications of the germicidal source to disperse the germicide therefrom. As an example, in embodiments in which the germicidal source is a pulsed discharge lamp, components 148 may include energy storage element/s, trigger voltage circuitry and pulse duration circuitry. Regardless of the type of germicidal source used and its specification, components 148 will generally include power circuitry, a user interface and optionally a battery. If one or more operations of germicidal source 142 are computer-operated, components 148 may further include a processor and program instructions for performing the computer-operated tasks.

As noted above, air moving device 146 serves to draw in air from an ambient of base 144. In general, disinfection apparatus 140 includes one or more air inlets such that air moving device 146 can readily access and draw in air from an ambient of base 144. The air inlets may be along the sidewalls, top and/or bottom of the exterior containment unit of base 144. In addition or alternatively, the exterior containment unit of base 144 may not enclose the bottom of base 144 extending between wheels 149 and the lack of enclosure may serve as an air inlet. In any case, air moving device 146 may include any device configured to cause air to flow, including but not limited to a fan, pump or a turbine. In addition to having air inlets along base 144 for air moving device 146 to access, disinfection apparatus 140 is configured to route air drawn in from the air moving device to germicidal source 142. The configurations of disinfection apparatus 140 to affect such action may include having air moving device 146 arranged at the base of germicidal source 142 and configured to expel the drawn-in air upward. In other cases, disinfection apparatus 140 may include a duct between air moving device 146 and a base of germicidal source 142.

In addition to air moving device 146 and components 148, base 144 may include additional components for the operation of disinfection apparatus 140. Example features include but are not limited to alignment markers, object movement mechanisms, a power cord, one or more batteries, a user interface, ozone filters and germicidal dose sensors. Descriptions of such features are referenced from above as discussed in reference to disinfection apparatus 50 of FIG. 3 and are not reiterated for disinfection apparatus 140 for the sake of brevity. In some cases, disinfection apparatus 140 may be a room disinfection device and, thus, may include one or more features commonly associated with such devices. Example features include but are not limited to automated movement of disinfection apparatus 140, automated movement of germicidal source 142 relative to base 140, wheels and/or a handle to affect portability of the device, configurations for remotely starting the disinfection apparatus, motion or occupancy sensors and door sensors.

Additional example features include germicidal source 142 arranged within disinfection apparatus 140 to distribute a germicide approximately 360° around the source and/or to a region approximately 2 feet to approximately 4 feet from a floor of a room. In addition or alternatively, disinfection apparatus 140 may include configurations to distribute an effective amount of germicide to achieve at least a 2-log reduction in bacterial contamination on surfaces within a room or area that are greater than 1 meter or even 2 or 3 meters from the germicidal source. For example, disinfection apparatus 140 may be configured to project a germicide from germicidal source 142 at a power flux of at least approximately 1.0 W/m$^2$. Descriptions of the aforementioned features are referenced from above as discussed in reference to features commonly associated with room disinfection devices and are not reiterated for disinfection apparatus 140 for the sake of brevity.

Figure 13:
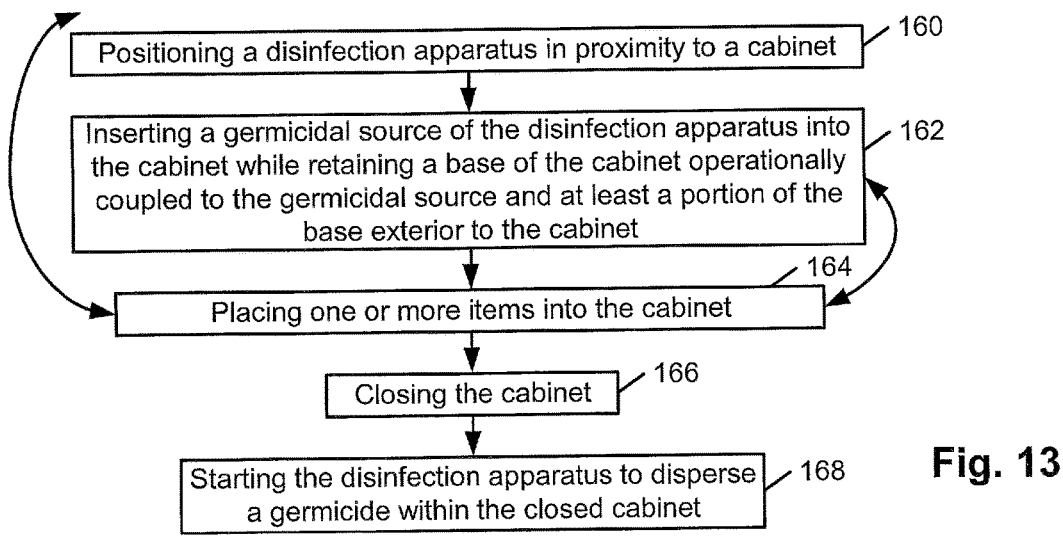
FIG. 13 illustrates an example flowchart of another method for disinfecting one or more objects in a cabinet.

A method for disinfecting one or more items in a cabinet that enables a germicidal source to be inserted into the cabinet while retaining at least a portion of a base supporting the germicidal source exterior to the cabinet is shown in the flowchart depicted in FIG. 13. System 150 resulting from performing such a method with cabinet 120, disinfection apparatus 140 and wheelchair 138 of FIG. 11 is shown in FIG. 12. As set forth in blocks 160 and 162 of FIG. 13, a method of disinfecting one or more items in a cabinet may include positioning a disinfection apparatus in proximity to a cabinet and inserting a germicidal source of the disinfection apparatus into the cabinet such that at least a portion of the base is retained exterior to the cabinet and is operationally coupled to the germicidal source. The result of such actions performed with cabinet 120 and disinfection apparatus 140 is shown in FIG. 12 with base 144 of disinfection apparatus 140 arranged within voided space 130 and germicidal source 142. Germicidal source 142 is depicted in dashed lines to indicate it is encased within cabinet 120. Although port 124 is shown in FIG. 12 around the base of germicidal source 142 at the top of base 144, port 124 may alternatively be arranged around a portion of base 144 as long at least a portion of base 144 is retained exterior to cabinet 120.

In some cases, the steps of blocks 160 and 162 of positioning a disinfection apparatus in proximity to a cabinet and inserting a germicidal source of the disinfection apparatus into the cabinet may include wheeling the disinfection apparatus into the appropriate positions relative to the cabinet. In other cases, the steps of blocks 160 and 162 of positioning a disinfection apparatus in proximity to a cabinet and inserting a germicidal source of the disinfection apparatus into the cabinet may involve a person carrying the disinfection apparatus and placing it is appropriate positions relative to the cabinet. In either case, the step of block 162 of inserting a germicidal source of the disinfection apparatus into the cabinet may, in some embodiments, including closing the cabinet around the disinfection apparatus and, in some embodiments, may include sealing the cabinet around the disinfection apparatus. As noted above, the disinfection apparatuses considered for the systems and methods disclosed herein may be, in some cases, configured to be independently operational from the cabinet. In other embodiments, however, a disinfection apparatus may need to be coupled to a power source through the cabinet in order to operate. In either case, the methods disclosed herein for disinfecting item/s in a cabinet, including the method outlined in FIG. 13, may, in some embodiments, include connecting the disinfection apparatus to a power source through the cabinet. Such a process may be generally conducted any time the disinfection apparatus is in an appropriate position for the connection to be made, such as prior to, during or subsequent to inserting the germicidal source of the disinfection apparatus into the cabinet.

As further shown in blocks 164 and 166 of FIG. 13, a method for disinfecting one or more objects in a cabinet may include placing one or more items into the cabinet and closing the cabinet. The result of such actions performed with cabinet 120 and wheelchair 138 is shown in FIG. 12 with wheelchair 138 arranged in interior space 132 of cabinet 120 and door 126 closed. Wheelchair 138 is depicted in dashed lines to indicate it is behind closed door 126. The doubled arrow line between blocks 162 and 164 indicates that either process may be conducted prior to the other or they may be performed at substantially the same time. The doubled arrow line between block 164 and the space above block 160 indicates that the placement of item/s into the cabinet may be conducted prior to positioning the disinfection apparatus in proximity to the cabinet or they may be performed at substantially the same time. In any case, the process of block 166 of closing the cabinet may be performed by closing the door of the loading port after the process of block 164 of placing the one or more items into the cabinet. In addition, the process of block 166 includes closing the port configured to receive the germicidal source after the germicidal source is inserted therein.

Subsequent to closing the cabinet with the germicidal source and the one or more items to be disinfected arranged therein and at least a portion of the base of the disinfection apparatus exterior to the cabinet, the method outlined in FIG. 13 includes starting the disinfection apparatus to disperse a germicide within the closed cabinet as denoted in block 168. The process of starting operation of the disinfection apparatus may be conducted at a user interface of the disinfection apparatus, at a user interface of the cabinet or via a remote user interface (i.e., a user interface remote to the disinfection apparatus and the cabinet). In any case, although not shown in FIG. 13, the method outlined therein includes terminating operation of the device and subsequently removing one or more of the items loaded therein and/or removing the germicidal source from the cabinet. The termination process may include any of the operations described in reference to blocks 20, 30 and 32 of FIG. 1. Descriptions of such operations are referenced from above as discussed in reference to FIG. 1 and are not reiterated for the method outlined in FIG. 13 for the sake of brevity.

The result of performing the step outlined in block 168 of FIG. 13 for system 150 of FIG. 12, specifically starting operation of disinfection apparatus 140 with germicidal source 142 arranged interior to cabinet 120 and at least a portion of base 144 exterior to cabinet 120, is shown in FIG. 12 with germicidal source projecting germicide 158 into the interior of cabinet 120. The dispersal of germicide 158 may generally depend on the configurations of germicidal source 142, but in cases in which germicidal source 142 is a germicidal light source, reflective materials along the sidewalls, ceiling and/or floor of the interior of cabinet 120 may aid in the distribution of germicidal light in the cabinet. As shown in FIG. 12, the operation of disinfection apparatus 140 also causes air moving device 146 to drawn in air 154 from the exterior ambient of base 144 and, as a result, exhaust 156 is discharged from cabinet 120 through air vents 128. A benefit of the configurations of cabinet 120 and disinfection apparatus 140 as well as performing the method outlined in FIG. 13 with cabinet 120 and disinfection apparatus 140 is that heat generated in the cabinet during a disinfection cycle may be removed from the cabinet without the use of an auxiliary air circulation system added to the cabinet. In particular, the systems, cabinets and methods shown and described in reference to FIGS. 11-14 allow relatively cool air to be drawn in from an external ambient of a cabinet via the base of a disinfection apparatus.

An alternative cabinet configuration which may be used for the methods disclosed herein and, particularly for use in the method outlined in FIG. 13, is shown in FIG. 14. In particular, FIG. 14 illustrates cabinet 160 having a different configuration than cabinet 120 of FIG. 11, namely the location of the port to receive a germicidal source of a disinfection apparatus, the location of the air vents and the configuration of the voided space. All other possible features of cabinet 160 may be the same as described for cabinet 120 of FIG. 11. Descriptions of the possible features of cabinet 130 are referenced for cabinet 160 and are not reiterated for the sake of brevity. As shown in FIG. 14, cabinet 160 may include port 174 arranged along a sidewall of exterior structure 172. Such placement of port 174 may be advantageous for receiving a germicidal source of a disinfection apparatus having a germicidal source facing or extending sideways from a base of the disinfection apparatus (i.e., rather than having a germicidal source extending up from a top surface of a base of a disinfection apparatus). As denoted by the arrowed lines along the periphery of port 174, port 174 may include an adjustable periphery such that the periphery of the port may be widened to allow an item of a particular size to be easily inserted therethrough, such as a germicidal source of a disinfection apparatus and potentially a casing around the germicidal source. As shown in FIG. 14, port 174 may, in some embodiments, be substantially flush with the exterior surface of exterior structure 172. In other cases, however, port 174 may be inset or extend out of exterior structure 172. Inset or flush ports may also be considered for port 124 of cabinet 120 depicted in FIG. 11.

Cabinet 160 further includes voided space 176 below port 174. Voided space 176 is configured to accommodate a portion of a base of a disinfection apparatus that supports a germicidal source to be inserted into port 174, particularly when the germicidal source does not extend past the confines of the base supporting it. The depth of the indentation of voided space 176 relative to the side of exterior structure 172 comprising port 174 may generally vary and, in some cases, may depend on the dimensional characteristics of the disinfection apparatus intended to be used with cabinet 160 for the disinfection of item/s therein. In some cases, however, cabinet 160 may not have voided space 176 below port 174. In other words, the portion of exterior structure 172 comprising port 174 of may alternatively extend down to the bottom of the cabinet such that there is no indentation in cabinet 160 below port 174. Such a configuration may be advantageous in embodiments in which a disinfection apparatus having a germicidal source that extends past the confines of the base supporting it is used with the cabinet to disinfection item/s therein.

Although port 174 is shown on an upper portion of an end of exterior structure 172, the location of port 174 need not be so restricted. In particular, port 174 may be alternatively arranged along a front facing or back facing side of cabinet 160 or even the end of cabinet 160 adjacent door 126. In addition or alternatively, port 174 may be arranged along a lower portion of exterior structure 172 in some cases. In some embodiments, it may be advantageous for portion 174 (as well as for port 124 of cabinet 120 in FIG. 11) to be arranged at least 12 inches above a floor of a space upon which the cabinet is arranged. In particular, cabinets 160 and 120 are intended to be used with disinfection apparatuses having germicidal sources extending out from the bases supporting them and bases of portable disinfection apparatuses, particularly portable room disinfection devices, generally have a base height of at least a foot. As such, placing ports 174 and 124 along cabinets 160 and 120 at least 12 inches above a floor of a space upon which the cabinets are arranged may increase the compatibility of the cabinet to be used with a portable disinfection apparatus, particularly a portable room disinfection apparatus.

Although cabinets 120 and 160 are respectively depicted in FIGS. 11 and 14 show ports 124 and 174 at one end of the cabinets, the location of ports 124 and 174 are not necessarily so limited. In particular, cabinets 120 and 160 may be configured to have ports 124 and 174 arranged closer to a midpoint along a length of the cabinets and, in some cases, substantially at such midpoints. In such cases, cabinet 120 and/or 160 modified in such a manner may include multiple areas to load and disinfect items and/or include moveable partitions to section off multiple areas of the cabinets, similar to the description of the cabinets shown in FIGS. 4-8.

The term "storage medium", as used herein, refers to any electronic medium configured to hold one or more set of program instructions, such as but not limited to a read-only memory, a random access memory, a magnetic or optical disk, or magnetic tape. The term "program instructions", as used herein, refers to commands within software which are configured to perform a particular function. Program instructions may be implemented in any of various ways, including procedure-based techniques, component-based techniques, and/or object-oriented techniques, among others. Program instructions may be transmitted over or on a carrier medium such as a wire, cable, or wireless transmission link.

It will be appreciated to those skilled in the art having the benefit of this disclosure that this invention is believed to provide support structures, systems, cabinets and methods for disinfecting objects. Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims. The term "approximately" as used herein refers to variations of up to +/−5% of the stated number.

What is claimed is:

1. A cabinet, comprising:
   a first port having a dimensionally adjustable periphery that is configured to conform to a periphery of an item partially inserted into the first port to seal the first port against the inserted item;
   a second port having a door; and
   one or more air vents extending between an interior of the cabinet and an exterior of the cabinet, wherein at least a majority portion of interior sidewalls of the cabinet comprise a material that exhibits greater than 85% reflectance to at least ultraviolet light and/or visible violet-blue light.

2. The cabinet of claim 1, wherein at least a majority portion of an interior ceiling of the cabinet comprise a material that exhibits greater than 85% reflectance to at least ultraviolet light and/or visible violet-blue light.

3. The cabinet of claim 1, wherein at least a majority portion of an interior flooring of the cabinet comprise a material that exhibits greater than 85% reflectance to at least ultraviolet light and/or visible violet-blue light.

4. The cabinet of claim 1, wherein the first port is arranged along a wall of the cabinet that is parallel with a floor of a space in which the cabinet is arranged.

5. The cabinet of claim 1, wherein the first port is along a wall of the cabinet that is perpendicular with a floor of a space in which the cabinet is arranged.

6. The cabinet of claim 1, wherein the first port is arranged at least 12 inches above a floor of a space upon which the cabinet is arranged.

7. The cabinet of claim 1, wherein the one or more air vents are arranged along an upper portion of the cabinet.

8. The cabinet of claim 1, wherein the cabinet is arranged on a floor of a space suitable for human occupancy, and wherein the door extends to a floor of the cabinet or the floor of the space.

9. The cabinet of claim 1, wherein the cabinet is readily collapsible and reconstructable.

10. The cabinet of claim 1, wherein the cabinet comprises an interior void of at least 20 ft$^3$ accessible by the second port.

11. The cabinet of claim 1, further comprising a germicidal dose sensor within the interior of the cabinet.

12. The cabinet of claim 1, wherein the dimensionally adjustable periphery of the first port comprises an elastic ring, an adjustable clamp or Velcro straps.

13. The cabinet of claim 1, wherein the one or more air vents comprise germicide filters.

14. The cabinet of claim 1, further comprising an occupancy sensor within the interior of the cabinet.

15. The cabinet of claim 1, further comprising a sensor to monitor movement of the door.

16. The cabinet of claim 1, further comprising one or more support structures arranged within the interior of the cabinet to hold objects.

17. The cabinet of claim 1, wherein a depth of the cabinet is between approximately 2 feet and approximately 5 feet.

18. The cabinet of claim 1, wherein a length of the cabinet is between approximately 6 feet and approximately 8 feet.

19. A cabinet, comprising:
    a first port having a dimensionally adjustable periphery that is configured to conform to a periphery of an item partially inserted into the first port to seal the first port against the inserted item, wherein the first port is arranged along an exterior wall of the cabinet that is parallel with a floor of a space in which the cabinet is arranged;
    a second port having a door;
    an interior void of at least 20 ft$^3$ accessible by the second port; and
    one or more air vents extending between an interior of the cabinet and an exterior of the cabinet.

20. The cabinet of claim 19, further comprising one or more support structures arranged within the interior of the cabinet to hold objects.

21. The cabinet of claim 19, wherein the first port is arranged at least 12 inches above the floor of the space upon which the cabinet is arranged.

22. A cabinet, comprising:
    a first port, wherein a portion of the cabinet adjoining the first port comprises a split starting at and extending away from an edge of the first port;
    respective mating parts of a fastener respectively disposed along opposing sections of the portion of the cabinet on respective sides of the split, wherein the portion of the cabinet is configured such that at least one of the opposing sections may be:
        moved away from the other opposing section to widen the first port; and
        moved toward the other opposing section such that the respective mating parts of the fastener are joined; and
    a second port having a door.

23. The cabinet of claim 22, wherein at least one of the opposing sections comprises a pliable material.

24. The cabinet of claim 22, wherein at least one of the opposing sections comprises a rigid material.

25. The cabinet of claim 22, wherein the portion of the cabinet is above the first port.

26. The cabinet of claim 22, wherein the first port is arranged at least 12 inches above a floor of a space upon which the cabinet is arranged.

27. The cabinet of claim 22, wherein the cabinet comprises an interior void of at least 20 ft$^3$ accessible by the second port.

28. The cabinet of claim 22, wherein the fastener is a zipper or a Velcro strap.

29. The cabinet of claim 22, wherein the fastener is a snap, a magnet, a hook and loop fastener or a clamp.

30. The cabinet of claim 22, wherein the fastener is a door latch.

31. The cabinet of claim 22, further comprising one or more additional sets of respective mating parts of one or more additional fasteners, wherein the one or more additional sets of respective mating parts are respectively disposed along the opposing sections of the portion of the cabinet.

32. The cabinet of claim 22, wherein at least a majority portion of interior sidewalls of the cabinet, at least a majority portion of a ceiling of the cabinet and/or at least a majority portion of a flooring of the cabinet comprise a material that exhibits greater than 85% reflectance to at least ultraviolet light and/or visible violet-blue light.

33. The cabinet of claim 22, wherein the first port is arranged along a wall of the cabinet that is parallel with a floor of a space in which the cabinet is arranged.

34. The cabinet of claim 22, wherein the first port is arranged along a wall of the cabinet that is perpendicular with a floor of a space in which the cabinet is arranged.

35. The cabinet of claim 22, further comprising one or more air vents extending between an interior of the cabinet and an exterior of the cabinet.

36. The cabinet of claim 22, wherein the cabinet is arranged on a floor of a space suitable for human occupancy, and wherein the door extends to a floor of the cabinet or the floor of the space.

37. The cabinet of claim 22, further comprising one or more support structures arranged within an interior of the cabinet to hold objects.

* * * * *